US008414475B2

(12) United States Patent
Sholev

(10) Patent No.: US 8,414,475 B2
(45) Date of Patent: Apr. 9, 2013

(54) CAMERA HOLDER DEVICE AND METHOD THEREOF

(75) Inventor: Mordehai Sholev, Amikam (IL)

(73) Assignee: M.S.T. Medical Surgery Technologies Ltd, Yoqneam (IL)

( * ) Notice: Subject to any disclaimer, the term of this patent is extended or adjusted under 35 U.S.C. 154(b) by 799 days.

(21) Appl. No.: 11/874,576

(22) Filed: Oct. 18, 2007

(65) Prior Publication Data

US 2008/0091066 A1 Apr. 17, 2008

Related U.S. Application Data

(63) Continuation of application No. PCT/IL2006/000478, filed on Apr. 20, 2006.

(60) Provisional application No. 60/672,010, filed on Apr. 18, 2005, provisional application No. 60/705,199, filed on Aug. 4, 2005, provisional application No. 60/716,953, filed on Sep. 15, 2005, provisional application No. 60/716, 951, filed on Sep. 15, 2005.

(51) Int. Cl.
*A61B 1/00* (2006.01)

(52) U.S. Cl. ........................................ 600/114; 600/102

(58) Field of Classification Search .................. 600/102, 600/114; 606/1, 130
See application file for complete search history.

(56) References Cited

U.S. PATENT DOCUMENTS

| 4,955,891 | A | * | 9/1990 | Carol | 606/130 |
| 5,269,305 | A | * | 12/1993 | Corol | 606/130 |
| 5,571,072 | A | * | 11/1996 | Kronner | 600/102 |
| 6,024,695 | A | | 2/2000 | Taylor | |
| 6,100,501 | A | | 8/2000 | von der Heyde | |
| 6,106,511 | A | * | 8/2000 | Jensen | 606/1 |
| 6,451,027 | B1 | * | 9/2002 | Cooper et al. | 606/130 |
| 6,714,841 | B1 | | 3/2004 | Wright et al. | |
| 6,723,106 | B1 | * | 4/2004 | Charles et al. | 606/130 |
| 6,946,812 | B1 | * | 9/2005 | Martin et al. | 318/567 |
| 7,313,430 | B2 | * | 12/2007 | Urquhart et al. | 606/130 |
| 7,674,270 | B2 | * | 3/2010 | Layer | 606/130 |

(Continued)

FOREIGN PATENT DOCUMENTS

JP 6063003 3/1994

OTHER PUBLICATIONS

International Search Report for PCT/IL2006/000478 filed Apr. 20, 2006.

(Continued)

*Primary Examiner* — Philip R Smith
*Assistant Examiner* — Rynae Boler
(74) *Attorney, Agent, or Firm* — Jordan IP Law, LLC; Todd A. Vaughn

(57) ABSTRACT

An improved interface between the surgeon and an endoscope system for laparoscopic surgery, holding a laparoscopic came and/or controlling an automated endoscope assistant includes at least one wireless transmitter with at least one operating key (12a). at least one wireless receiver (11), at least one conventional laparoscopy computerized system (15) loaded with conventional surgical instrument spatial location software, and conventional automated assistant maneuvering software, software loaded onto to the conventional laparoscopy system that enables a visual response to the depression of at least one key on the wireless transmitter as well as an interface with the conventional automated assistant maneuvering software so as to achieve movement of the endoscope, and at least one video screen (30).

8 Claims, 32 Drawing Sheets

U.S. PATENT DOCUMENTS

| | | | |
|---|---|---|---|
| 2002/0133174 A1* | 9/2002 | Charles et al. | 606/130 |
| 2004/0024387 A1* | 2/2004 | Payandeh et al. | 606/1 |
| 2004/0162564 A1* | 8/2004 | Charles et al. | 606/130 |
| 2004/0204627 A1 | 10/2004 | Furukawa | |
| 2005/0043718 A1* | 2/2005 | Madhani et al. | 606/1 |
| 2005/0162383 A1* | 7/2005 | Rosenberg | 345/156 |
| 2005/0171557 A1* | 8/2005 | Shoham | 606/130 |
| 2005/0273086 A1* | 12/2005 | Green et al. | 606/1 |
| 2006/0100501 A1 | 5/2006 | Berkelman et al. | |
| 2006/0167440 A1* | 7/2006 | Cooper et al. | 606/1 |
| 2008/0091066 A1 | 4/2008 | Sholev | |
| 2008/0091302 A1 | 4/2008 | Sholev | |

OTHER PUBLICATIONS

International Preliminary Report on Patentability published Oct. 23, 2007 for PCT/IL2006/000478 filed Apr. 20, 2006.

Written Opinion of the International Searching Authority published Oct. 18, 2007 for PCT/IL2006/000478 filed Apr. 20, 2006.

Response to Office Action dated Sep. 13, 2012 for U.S. Appl. No. 13/223,767.

Restriction requirement dated Aug. 17, 2012 for U.S. Appl. No. 11/874,534.

Office Action dated Jun. 14, 2012 for U.S. Appl. No. 13/223,767.

\* cited by examiner

CAMERA HOLDER DEVICE AND METHOD THEREOF

FIELD OF THE INVENTION

The present invention discloses a camera holder device and mechanism for laparoscopic surgery. The camera holder device is easily installed and disassembled, comfortable to use, not limiting the dexterity of the surgeon, having small physical dimension and inexpensive.

BACKGROUND OF THE INVENTION

In laparoscopic surgery, the surgeon performs the operation through small holes using long instruments and observing the internal anatomy with an endoscope camera. The endoscope is conventionally held by a camera assistant since the surgeon must perform the operation using both hands. The surgeon performance is largely dependent on the camera position relative to the instruments and on a stable image shown at the monitor; also the picture shown must be in the right orientation. The main problem is the difficulty for the assistant to keep the endoscope in the right spatial position, to hold the endoscope steadily, keeping the scene in the right orientation. To overcome these problems, several new technologies have been developed, using robots to hold the endoscope while the surgeon performs the procedure, e.g., Lapman, Endoassist etc. But these technologies are expensive, difficultly installed, uncomfortable to use, limiting the dexterity of the surgeon and having physical dimension much bigger that all operating tools. Relatively to the required action, they also move in big bounds with several arms movement. Another robot, LER (which was developed by the TIMC-GMCAO Laboratory) US. Patent application No. 200/6100501 Consists of a compact camera-holder robot that rests directly on the patient's abdomen and an electronic box containing the electricity supply and robot controllers. LER has relatively small dimensions but has a 110 mm diameter base ring that must be attached, or be very close to patient skin. This ring occupies place over the patient body limiting the surgeon activities: choosing the place of the other trocars, changing the surgeon to usual way of making the procedure, forcing sometimes the setup process to be as long as 40 minutes. Also the LER has only 3 degrees of freedom and have no ability to control the orientation of the picture shown to surgeon (the LER can not rotate the endoscope around its longitudinal axis).

Reference is made now to FIGS. 1a, 1b, 1c, presenting a schematic illustration of the prior art which describes these technologies.

Laparoscopic surgery is becoming increasingly popular with patients because the scars are smaller and their period of recovery is shorter. Laparoscopic surgery requires special training of the surgeon or gynecologist and the theatre nursing staff. The equipment is often expensive and not available in all hospitals. During laparoscopic surgery it is often required to shift the spatial placement of the endoscope in order to present the surgeon with the optimal view. Conventional laparoscopic surgery makes use of either human assistants that manually shift the instrumentation or alternatively robotic automated assistants (such as JP patent No. 06063003).

However, even the improved technologies are still limiting the dexterity of the surgeon and failing to provide four degrees of freedom. Another disadvantage of those technologies is the lack of ability to control the spatial position of an endoscope tube to any orientation during said laparoscopic surgery, such that the surgeon reaches any desired area within the working envelope in operated body.

Therefore, there is still a long felt need for a camera holder that would allow holding and controlling the endoscope steadily without limiting the dexterity of the surgeon and that will provide four degrees of freedom. Furthermore, there is still a long felt need for a camera holder that will provide the ability to control the spatial position of an endoscope tube to any orientation during said laparoscopic surgery, such that the surgeon reaches any desired area within the working envelope in operated body.

SUMMARY OF THE INVENTION

It is one object of the invention to disclose a camera holder, useful for laparoscopic surgery; wherein said camera holder is provided with means of manipulation in four degrees of freedom; further wherein said camera holder is provided with means of controlling the spatial position of an endoscope tube to any orientation during said laparoscopic surgery, such that said endoscope reaches any desired area within the working envelope in an operated body.

It is another object of the invention to disclose the camera holder as defined above, wherein said camera holder is adapted to have small physical dimension.

It is another object of the invention to disclose the camera holder as defined above, wherein said camera holder comprises:
  a. a housing (309); said housing is adapted to be connected and disconnected to said endoscope; said housing comprises:
    i. at least one zoom mechanism;
    ii. at least one endoscope rotation mechanisms;
  b. rotating DF (304); and
  c. sliding DF (305).

It is another object of the invention to disclose the camera holder as defined above, wherein said camera holder additionally comprises:
  a. motor house;
  b. means adapted to transmit movement to said zoom mechanism;
  c. means adapted to transmit movement to said endoscope rotation mechanism;
  d. means adapted to transmit movements to said endoscope rotating DF;
  e. means adapted to transmit movements to the sliding DF.

It is another object of the invention to disclose the camera holder as defined above, wherein said zoom mechanism is adapted to provide a zoom action; further wherein said endoscope rotation mechanism is adapted to rotate said endoscope about its long axis; further wherein said endoscope rotation mechanism and/or said zoom mechanism and/or said rotating DF and/or said sliding DF are adapted to be independent of other moving parts of said camera holder mechanism.

It is another object of the invention to disclose the camera holder as defined above, wherein said camera holder is disposable.

It is another object of the invention to disclose the camera holder as defined above, wherein said camera holder additionally comprises a quick release handle adapted to disassemble said endoscope out of said housing without changing any of said degrees of freedom.

It is another object of the invention to disclose the camera holder as defined above, wherein said camera holder additionally comprising a telescopic guide; said telescopic guide is adapted to provide said endoscope movement along said endoscope longitudinal axis.

It is another object of the invention to disclose the camera holder as defined above, additionally comprising:
a. a zoom ring (1);
b. orientation ring (3);
c. at least two cables 4a and 4b; said cables 4a and 4b are characterized by having length of $L_1$ and $L_2$;
d. a spring (5); said spring is characterized by having a resistance K; and
e. a basis ring (6);
wherein lengths of $L_1$, $L_2$ are changeable in conjunction with said spring's resistance K, thereby said orientation ring is moved relatively to said basis ring.

It is another object of the invention to disclose the camera holder as defined above, wherein said rotation mechanism comprises at least one cable; at least one worm gear; said cable is adapted to rotate said worm gear such that said endoscope is rotated.

It is another object of the invention to disclose the camera holder as defined above, wherein said rotation mechanism comprises at least one pulley block; said pulley block are adapted to control the spatial angular position of said endoscope.

It is another object of the invention to disclose the camera holder as defined above, wherein said camera holder additionally comprising means such that said camera holder is adapted to be portable.

It is another object of the invention to disclose the camera holder as defined above, wherein said means comprising (a) at least one adjustable arm; and (b) a basis comprising at least one motor; said adjustable arm couples said camera holder and said basis.

It is another object of the invention to disclose the camera holder as defined above, wherein said zoom mechanism is selected from a group comprising adjustment cable mechanism, parallelogram rods mechanism, a spring mechanism, a reduction force mechanism, rotating cable mechanism and a two springs zoom mechanism.

It is another object of the invention to disclose the camera holder as defined above, wherein said camera holder comprising a manipulating endoscope mechanism (1); a force carriage system (2); and a force source (3).

It is another object of the invention to disclose the camera holder as defined above, wherein said manipulating endoscope mechanism comprises:
a. at least one cable;
b. at least one spring; and
c. at least one rod;
said force carriage system comprises:
a. at least one cable;
b. at least one chain; and
c. at least one rod;
said force source comprises
a. at least one motor; and/or at least one actuator; at least one piston.

It is another object of the invention to disclose a method for controlling the spatial position of endoscope tube to any orientation in laparoscopic surgery, such that the surgeon reaches any desired area within the working envelope in operated body. The method comprises step selected inter alia from (a) obtaining a camera holder as defined above; (b) assembling said endoscope to said housing; and (c) controlling and manipulating said endoscope such that an optimal field view is obtained; wherein said step of controlling and manipulating said endoscope is providing said endoscope movement in four degrees of freedom.

It is another object of the invention to disclose the method as defined above, additionally comprising the step of zooming in and/or zooming out of said desired area such that more precisions is obtained.

It is another object of the invention to disclose the method as defined above, wherein said step of zooming in and/or zooming out additionally comprises the step of moving said endoscope along said endoscope longitudinal axis.

It is another object of the invention to disclose the method as defined above, additionally comprising the step of rotating said endoscope.

It is another object of the invention to disclose the method as defined above, additionally comprising the step of disassembling said endoscope to said housing.

It is another object of the invention to disclose the method as defined above, additionally comprising the step of controlling the rotation angle of said endoscope along said endoscope long axis.

It is another object of the invention to disclose the method as defined above, additionally comprising the step of selecting said zoom mechanism from a group comprising adjustment cable mechanism, parallelogram rods mechanism, a spring mechanism, a reduction force mechanism, rotating cable mechanism and a two springs zoom mechanism.

It is still an object of the invention to disclose the method as defined above, additionally comprising the step of adjusting said camera holder to be portable.

It is lastly an object of the invention to disclose the method as defined above, additionally comprising the step of disassembling the endoscope out of the zoom mechanism without changing any degree of freedom of the spatial position of said endoscope, by activating said endoscope independently of other moving parts of the mechanism, such that the entire system does not have to be re-positioned.

BRIEF DESCRIPTION OF THE FIGURES

In order to understand the invention and to see how it may be implemented in practice, and by way of non-limiting example only, with reference to the accompanying drawing, in which.

DETAILED DESCRIPTION OF THE EMBODIMENTS

The following description is provided so as to enable any person skilled in the art to make use of the invention and sets forth the best modes contemplated by the inventor of carrying out this invention. Various modifications, however, will remain apparent to those skilled in the art, since the generic principles of the present invention have been defined specifically to provide a camera holder mechanism for laparoscopic surgery.

The present invention provides a camera holder, useful for laparoscopic surgery. The camera holder is provided with means of manipulation in four degrees of freedom. The camera holder is provided with means of controlling the spatial position of an endoscope tube to any orientation during the laparoscopic surgery, such that the endoscope reaches any desired area within the working envelope in an operated body.

The present invention also provides a method for controlling the spatial position of endoscope tube to any orientation in laparoscopic surgery, such that the surgeon reaches any desired area within the working envelope in operated body. The method comprises step selected inter alia from (a) obtaining a camera holder mechanism as defined above; (b) assembling the endoscope to the housing; and (c) controlling and manipulating the endoscope such that an optimal field view is obtained;

The step of manipulating the endoscope is provided in four degrees of freedom.

The term "pulley" refers hereinafter to a wheel with a groove between two flanges around its circumference, the groove normally locates a rope, cable or belt. Pulleys are used to change the direction of an applied force, transmit rotational motion, or realize a mechanical advantage in either a linear or rotational system of motion.

The term "gimbal" refers hereinafter to a pivoted support that allows the rotation of an object about a single axis.

The term "small physical dimension" refers hereinafter to the physical dimensions of a human palm.

The term "four degrees of freedom" refers hereinafter to the four independent degrees of freedom illustrated in FIG. 5.

Figure 27:
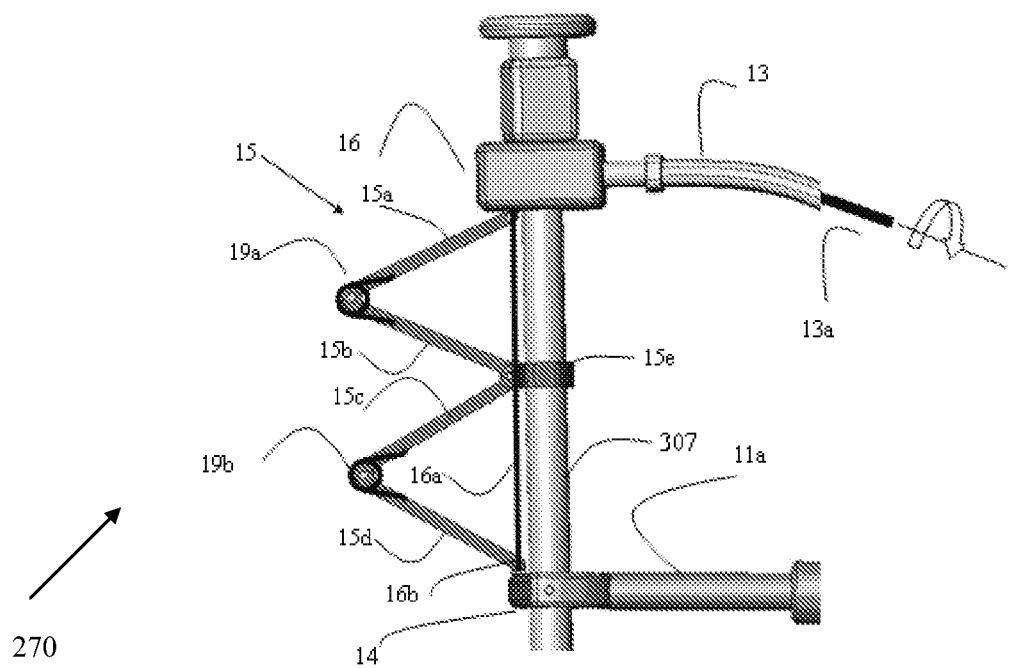
FIG. 27 presents the zoom mechanism, according to another embodiment of the present invention (the "two springs zoom mechanism")

The term "adjustment cable mechanism" refers hereinafter to the zoom mechanism described in FIG. 14;

The term "parallelogram rods mechanism" refers hereinafter to the zoom mechanism described in FIGS. 18a and 18b;

The term "spring mechanism" refers hereinafter to the zoom mechanism described in FIGS. 19a and 19b;

The term "a reduction force mechanism" refers hereinafter to the zoom mechanism described in FIG. 20;

The term "rotating cable mechanism" refers hereinafter to the zoom mechanism described in FIG. 23;

The term "two springs zoom mechanism" refers hereinafter to the zoom mechanism described in FIG. 27;

The term "zoom leading bars" refers hereinafter to the bars described in FIG. 25.

Figure 1A:
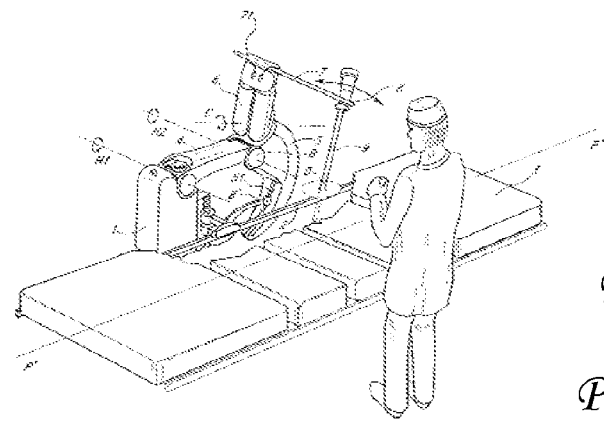
FIG. 1a, 1b, 1c present a schematic illustration of prior art technologies.
Figure 1C:
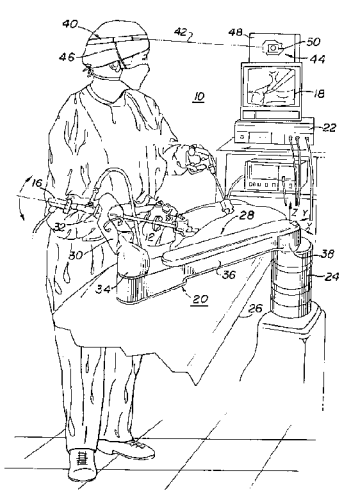
Figure 1B:
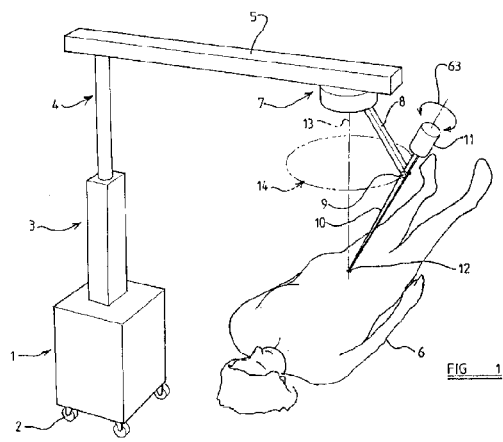
Figure 2:
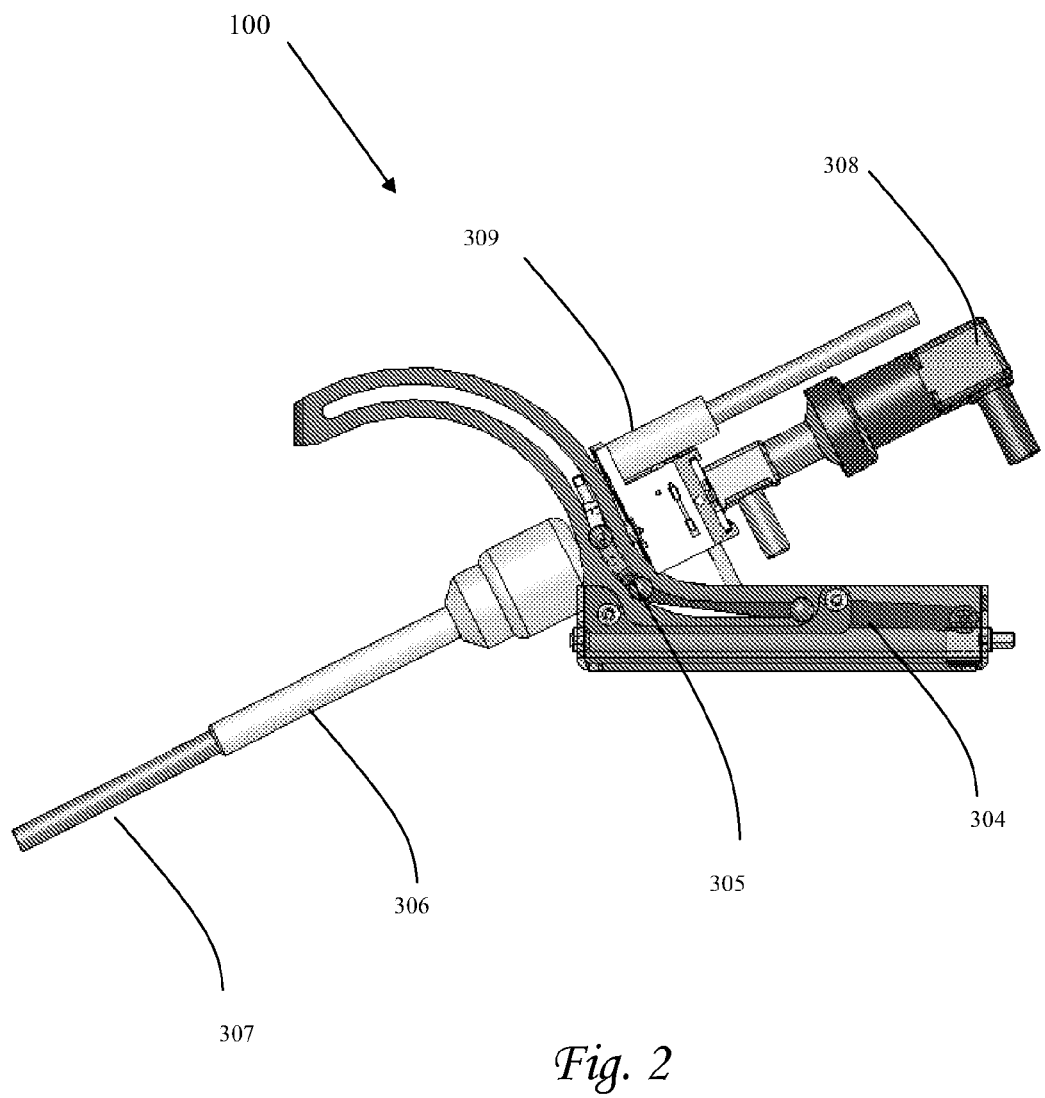
FIG. 2 is a schematic view of the camera holder.
Figure 3:
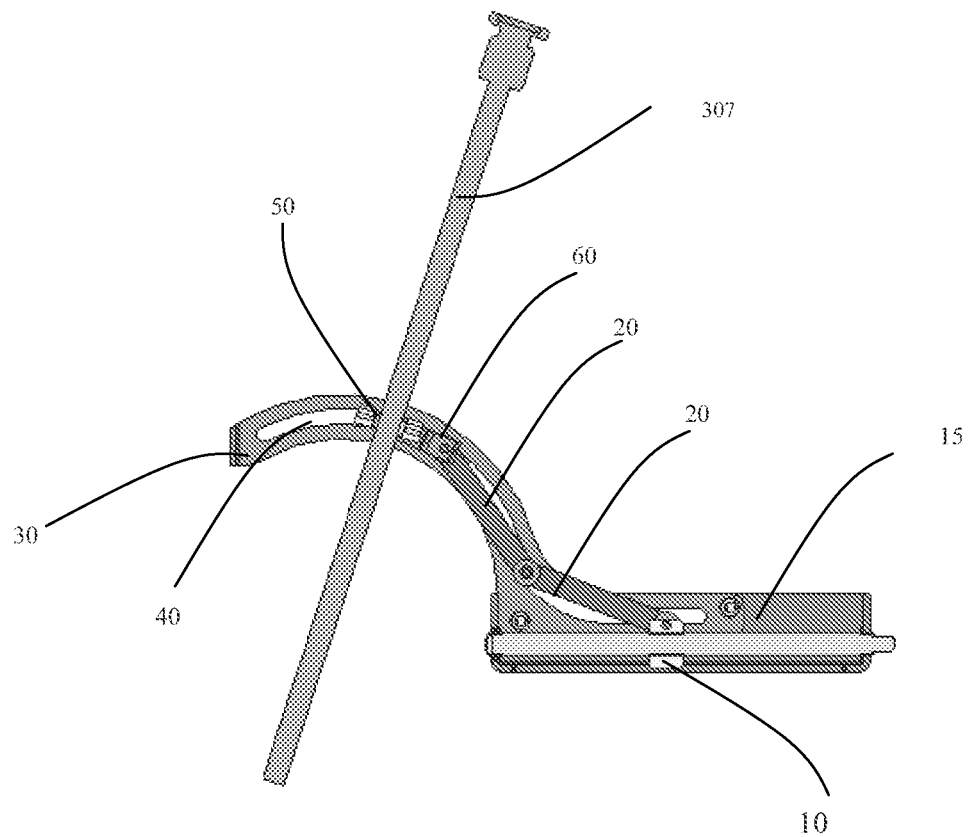
FIG. 3 is a schematic cut view of the camera holder.

Reference is made now to FIGS. 2 and 3 which illustrate the camera holder device 100.

As can be seen from FIG. 2, the camera holder 100 comprises a mechanism allowing degrees of freedom (DF) in the rotational direction (denoted hereinafter as rotating DF) 304, a mechanism allowing degrees of freedom (DF) in sliding (denoted hereinafter as sliding DF) 305 and housing 309. The housing 309 comprises a rotation and a zoom mechanism. The rotating DF 304, sliding DF 305 and housing 309 can be disposable. Camera 308, endoscope 307 and Trocar 306 can also be seen in FIG. 2. FIG. 2 illustrates the mechanism of the camera holder 100. The camera holder consists of two main components: the first part has an arc shape in which the endoscope can be driven back and forth and at the same time can be move from side to side (the sliding DF and the rotating DF); the second part 309 is characterized by zoom and endoscope rotation properties. The mechanism allows the moving and the positioning of the endoscope in the angles of 0°-90° back and forth and 0°-180° side to side.

As mentioned above, the camera holder consists of an arc shape housing which moves a gimbal (50) along an arc shape guide. The base of the arc includes a housing containing a lead screw (15) that moves a nut (10) through which the screw is threaded back and forth. The lead screw is constrained to remain in one position such that rotation of the screw moves the nut. The sliding DF is achieved by connecting the moving nut to the gimbal with links (20) that transfer the linear nut movement to the gimbal 50 resulting in its movement back and forth along the arc shaped guide. The lead screw housing (screw housing 30) is connected to another mechanism (the rotating DF) which rotates the first part from side to side around the longitudinal axis of the lead screw. This mechanism may also supply at the same time the movements needed to rotate the lead screw. This design allows the motors that move the first part to be connected from a distance preferably by flexible or articulated shafts. The separation is a very useful feature due to the fact that the presence of the mechanism becomes minor.

The zoom mechanism and the endoscope rotation mechanism are located in a same housing 309. This housing is connected to the gimbal 50 that slides in the arc. A spring is connected to the gimbal at one end and to the mechanisms housing at the other end not allowing the housing to move down. A wire is also connected to the gimbal at one end and to the mechanisms housing at the other end keeping a desired distance between the gimbal and the housing.

These mechanisms may be operated by flexible shaft 303 that is coupled to the motors located in the motor box, or by motors attached directly to the mechanisms axles.

The flexible shaft is connected to an axle of a worm gear. During zoom down the drum mechanically connected to the worm gear winds the wire up, so that the distance between the drum and the muff becomes shorter. When the motor stops moving, the spring keeps tension of the wire. The structure of the worm gear prevents the spring 185 from unsanctioned displacement of the transmission box. During zoom out movement the motor rotates in the opposite direction. The unwrapped wire lets the spring to extend. As a result the zoom box transmission rises.

Figure 3A:
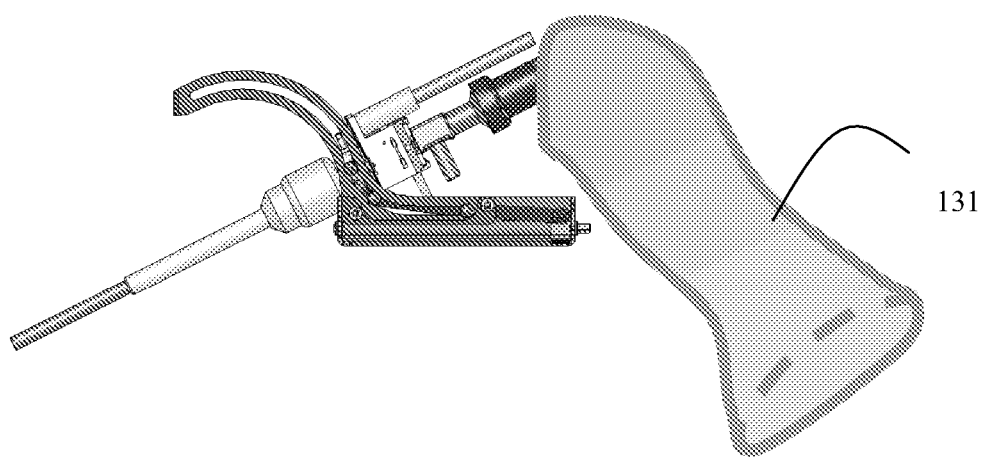
Figure 3B:
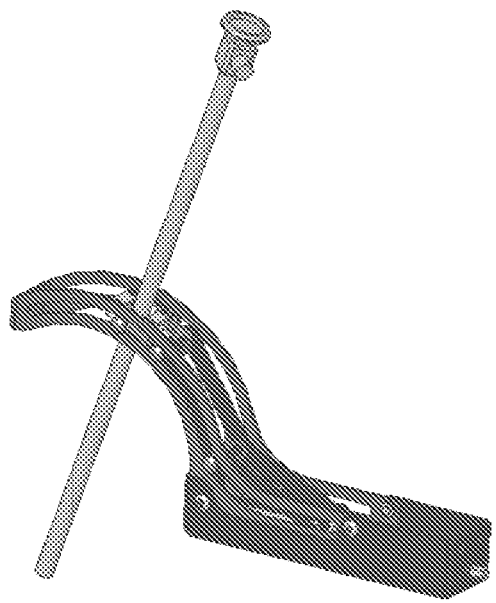
Figure 3C:
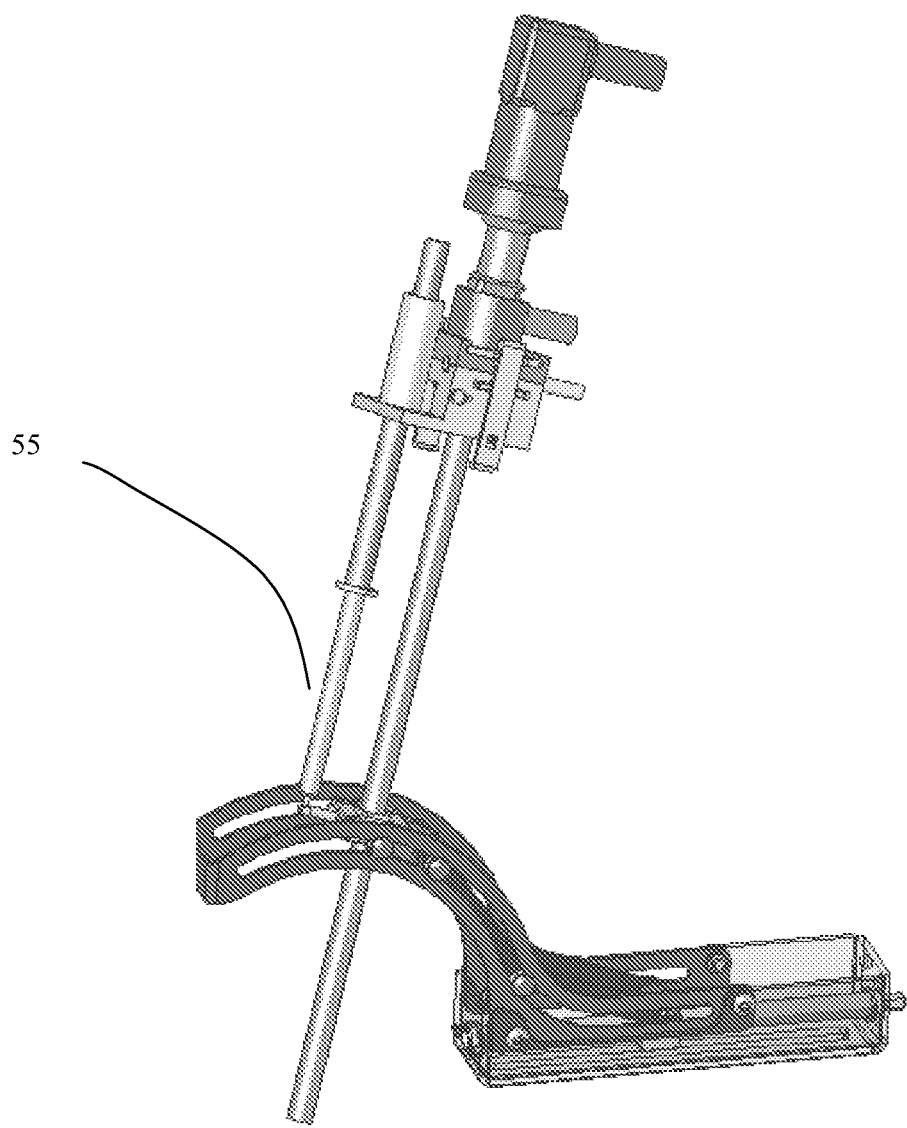
Figure 5:
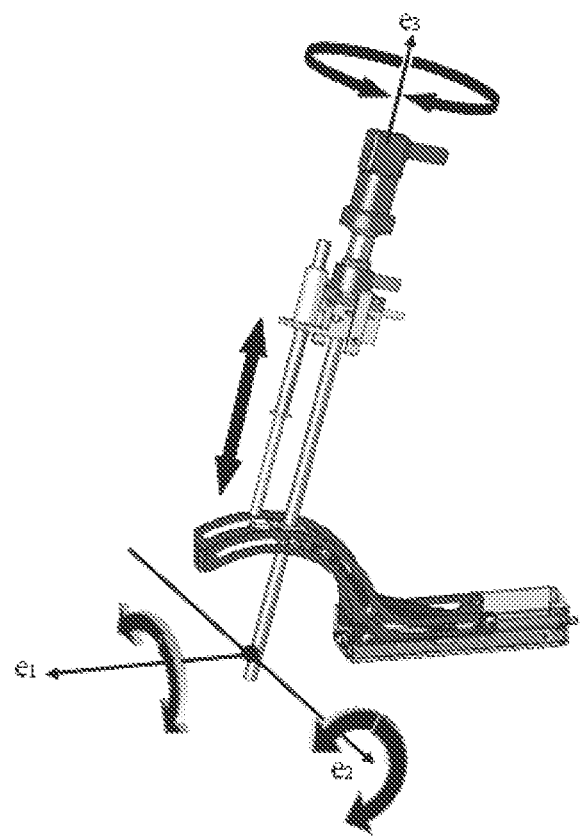
FIG. 5 schematically illustrates the four degrees of freedom of the mechanism.
Figure 6:
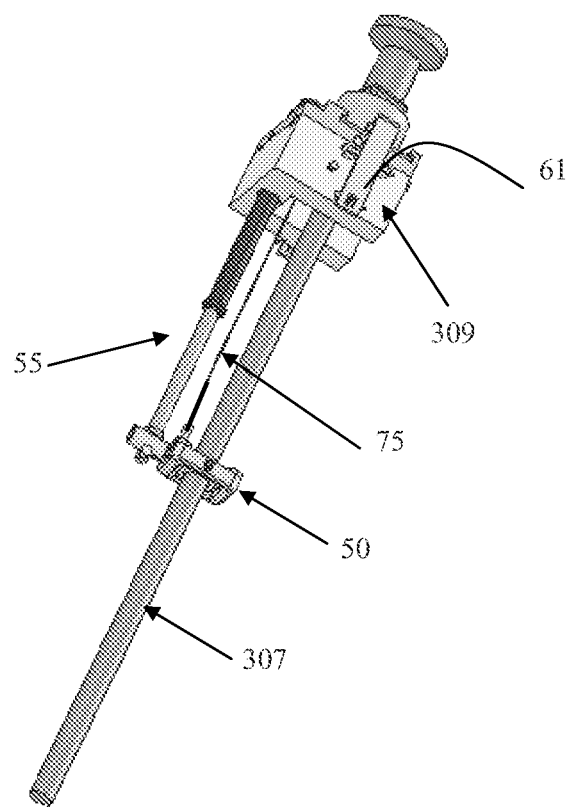
FIGS. 6 and 7 are schematic view of the telescopic guide.

The spring may be a part of Telescopic Guide 55 shown in FIGS. 3c, 5, 6.

Reference is made now to FIG. 3 illustrating a cut view of the first part. Rotating the lead screw causes linear movement of the moving nut. In the case where the moving nut 10 moves forward, it pushes the chain of links 20 that are connected to gimbal 50. The link movement is guided by tiny wheels that are placed in the curved guide way 40. The movement of the link is passed to the outer gimbal 50 directly via a connector 60 or like in FIG. 2 via another link 20. There is no limit in principle to the number of links except for the physical dimensions of the mechanism.

Reference is now made to FIG. 3a which schematically illustrates the camera holder which additionally comprises sterile sleeve 131 which covers the camera 308.

Reference is made now to FIG. 3b illustrating a different view of the entire mechanism. FIG. 3c additionally displays telescopic guide 55 in its stretched position.

Figure 4:
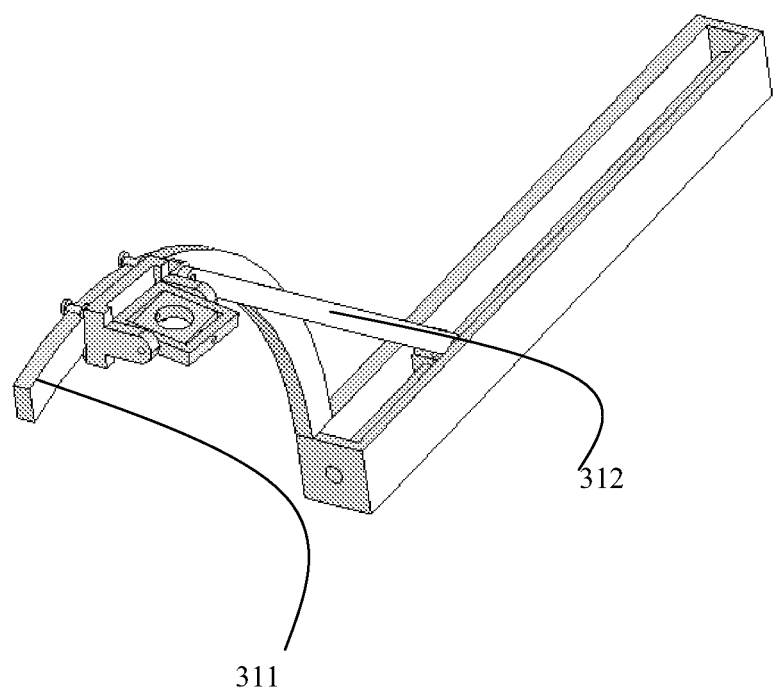
FIG. 4 schematically illustrates a mechanism with only one curved guide.

Reference is made now to FIG. 4 illustrating another realization of the mechanism using only one curved guide way 311, and a single chain of links 312. This structure has some more advantages: the whole mechanism is thinner and smaller and allows a faster connection and disconnection of the endoscope from the mechanism, for example in a case when cleaning of the endoscope lens is needed.

Reference is made now to FIG. 5 illustrating the mechanism's four degrees of freedom: rotation about axis e1 (provided by the rotating DF), rotation about axis e2 (provided by the sliding DF), rotation about axis e3 (provided by endoscope rotation mechanism) and zoom along axis e3.

Figure 7:
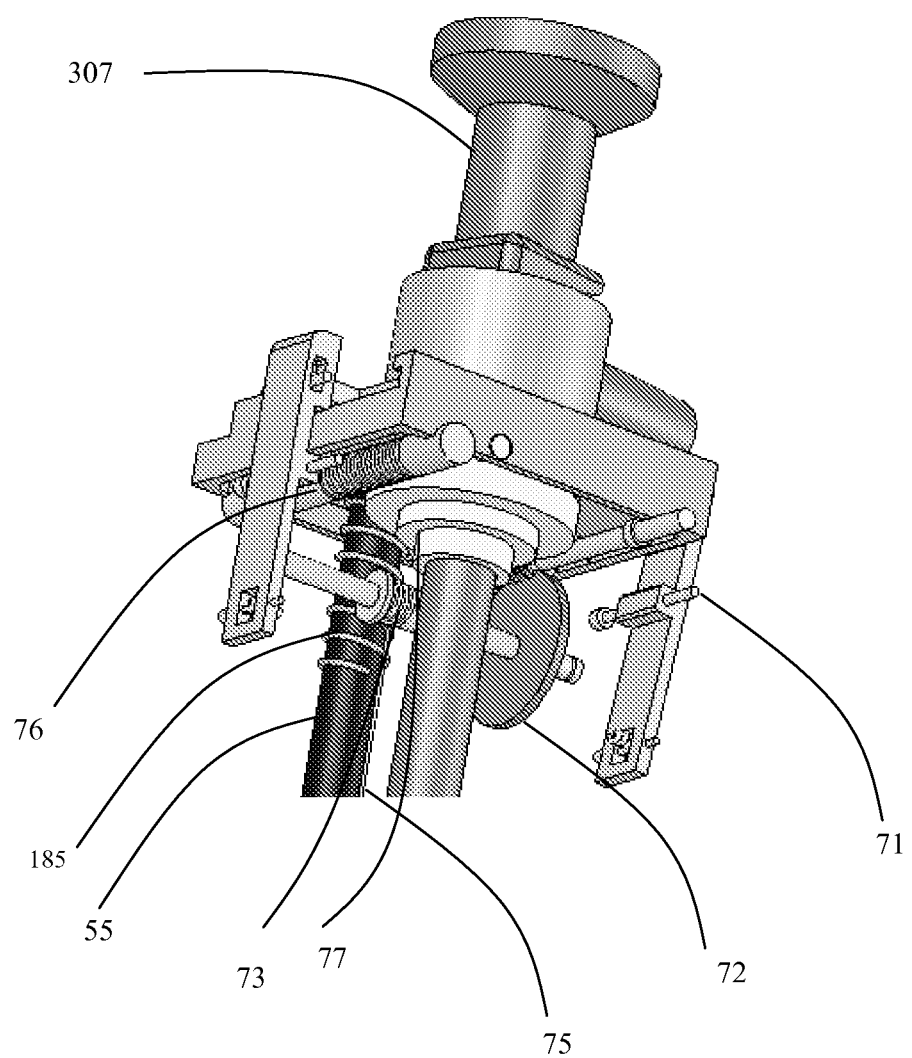

Reference is made now to FIGS. 6 and 7, illustrating the mechanism of the telescopic guide 55. The telescopic guide mechanism enables the movement of the endoscope to move in a zoom movement, where the endoscope moves along its longitudinal axis. Reference is made now to FIG. 6. FIG. 6 illustrates the connection between the housing 309 and the arc mechanism (shown for example in FIG. 3). The telescopic guide 55 connects the housing 309 to the gimbal (50). As explained above, the gimbal both slides along and moves with the arc when the arc rotates from side to side. While keeping a rigid connection with the gimbal (50), the telescopic guide enables the movement of the endoscope 307 in a zoom movement, where the endoscope moves along its longitudinal axis. As described in detail below, wire 75 connects gimbal (50) to a drum located within housing 309 (the drum is not visible in the view illustrated in FIG. 6). Rotation of the drum lengthens or shortens wire 75, drawing gimbal (50) up or down in the process. Endoscope 307 is locked in housing 309 and passes through the inner gimbal (50). A quick release handle 61 adapted to disassemble said endoscope out of said housing 309 without changing any of said degrees of freedom.

Reference is now made to FIG. 7, which shows the components of the zoom mechanism in detail. Worm gear 1 (denoted as 71) may be rotated clockwise or counter clockwise by a flexible shaft 303 (not shown in FIG. 7; see FIG. 8 below) or directly by a tiny motor. When worm gear 1 rotates it causes rotation of cog wheel 1 (denoted as 72).

Cog wheel 1 (72) has the same axle as drum 1 (73), such that when cog wheel 1 rotates, drum 1 rotates also and winds or unwinds (depending on the direction of the rotation) wire 75 that is wrapped around the drum. When the rotation results in unwinding of the wire, spring 185 contained in the telescopic guide 55 expands and pushes the housing up, increasing the distance between the gimbal (50) and the housing 309 resulting in "zoom out" movement. When the rotation results in winding of the wire, the distance between the gimbal (50) and the housing 309 shortens, resulting in "zoom in" movement.

FIG. 7 also shows the components of the mechanism that rotates the endoscope around its longitudinal axis. This mechanism comprises worm gear 2 (denoted as 76) and cog wheel 2 (denoted as 77). Worm gear 2 (76) may be rotated clockwise or counterclockwise by a flexible shaft (not shown in FIG. 7; see FIG. 8 below) or directly by a tiny motor. When worm 2 (76) rotates it causes rotation of cog wheel 2 (77). In one embodiment of this invention, cog wheel 2 may be attached directly to the endoscope and held in place by frictional forces. When cog wheel 2 (77) rotates the endoscope rotates in the same direction.

Figure 8A:
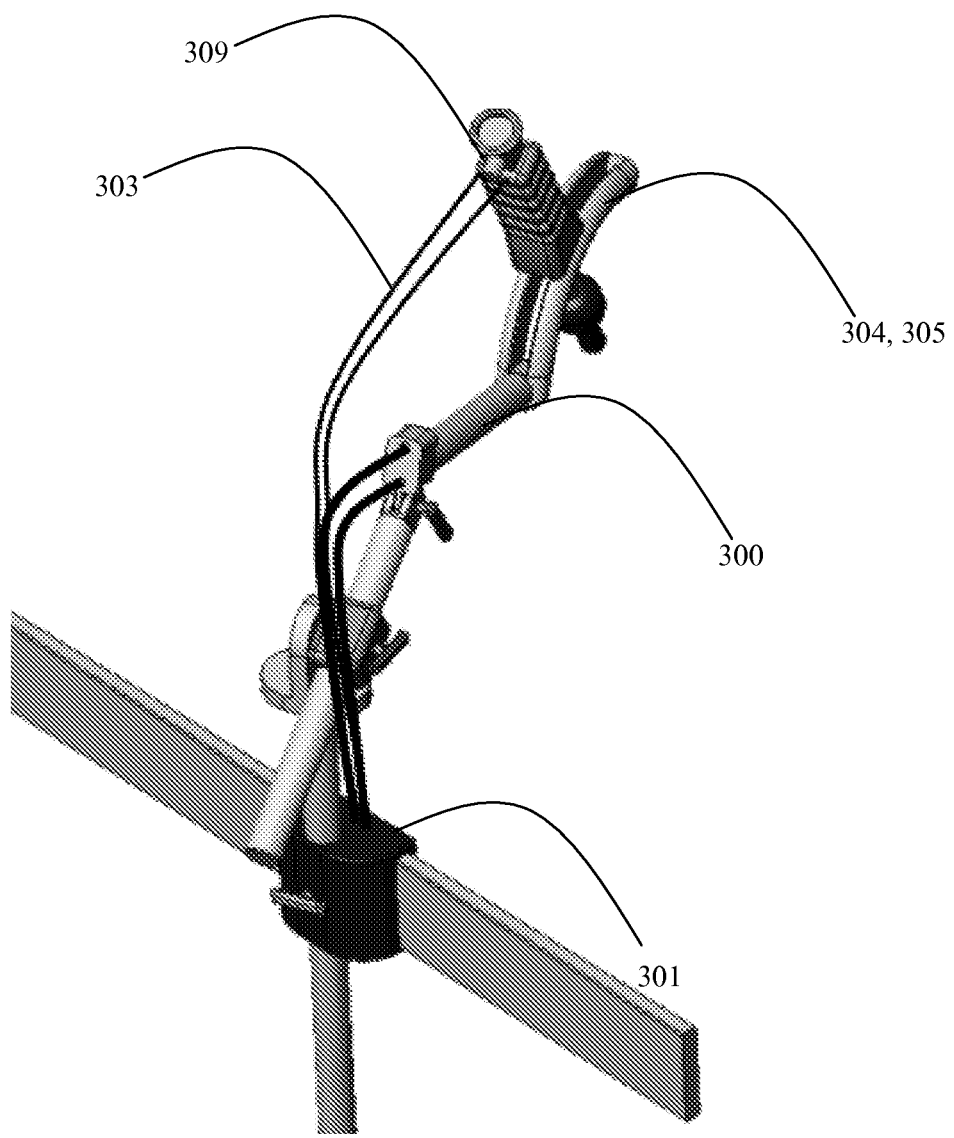
FIG. 8a, 8b, 8c schematically present an illustrating example of a camera holder mechanism for laparoscopic surgery.
Figure 8B:
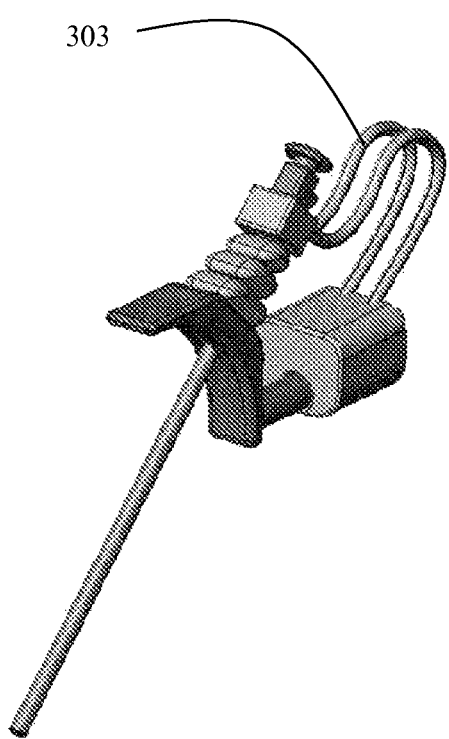
Figure 8C:
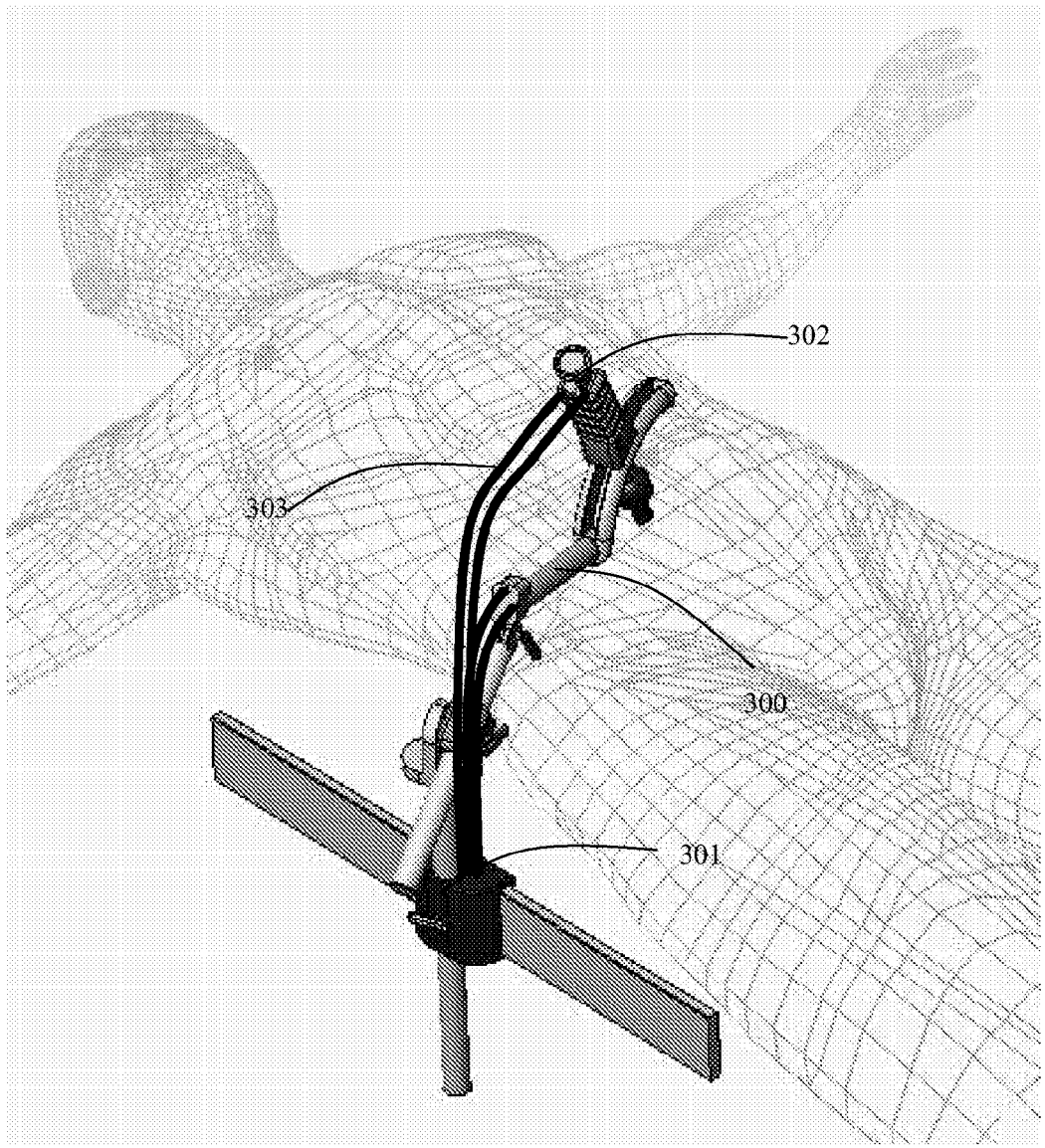

Reference is made now to FIGS. 8a, 8b, 8c, which illustrate an example of a camera holder mechanism for laparoscopic surgery. The camera holder comprises a motor house 301 and a zoom and rotation mechanism 309, a sliding DF (305), a rotating DF (304), arms for pulling the slider (300) and tubes with flexible wire that transmit the rotational moment to the component of the zoom mechanism (303).

Figure 9:
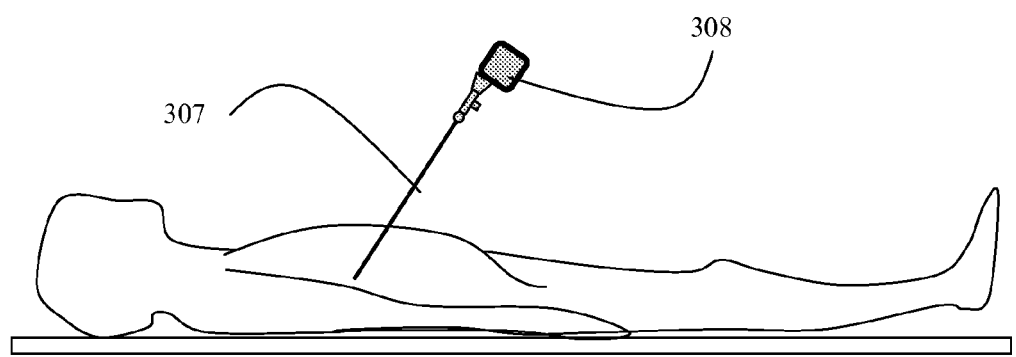
FIG. 9 illustrates the way in which the endoscope is inserted through a small incision in the abdomen or chest.

The present invention generally relates to means and methods of controlling an endoscope system for laparoscopic surgery, in which the endoscope (into which a camera 308 is coupled) is inserted through a small incision in the abdomen as illustrated in FIG. 9.

It is another object of the present invention to present a novel means for controlling the spatial position of endoscope tube in laparoscopic surgery. The present device is inexpensive, easy to install and to disassemble, comfortable to use, does not limit the dexterity of the surgeon, and has small physical dimensions.

The small size of present invention is achieved by applying the following steps:
1. separating the moving parts from the motors and transmitting the motor power by cable and/or shafts means;
2. applying a linear zoom mechanism, allowing a full range of zoom action, independent of other moving parts in the mechanism, e.g. not like other robots that achieve the linear zoom action by a combined movement of the robot arms;

3. obtaining a rotational mechanism that rotates the endoscope about its long axis, independently of other moving parts of the mechanism, e.g., not like other robots that does not have the ability to compensate un wanted rotational movements (for example LER), or by a combined movement of the robot arms that produce big movements in order to achieve small rotations (AESOP Endoassist Lap-Man).

Figure 10:
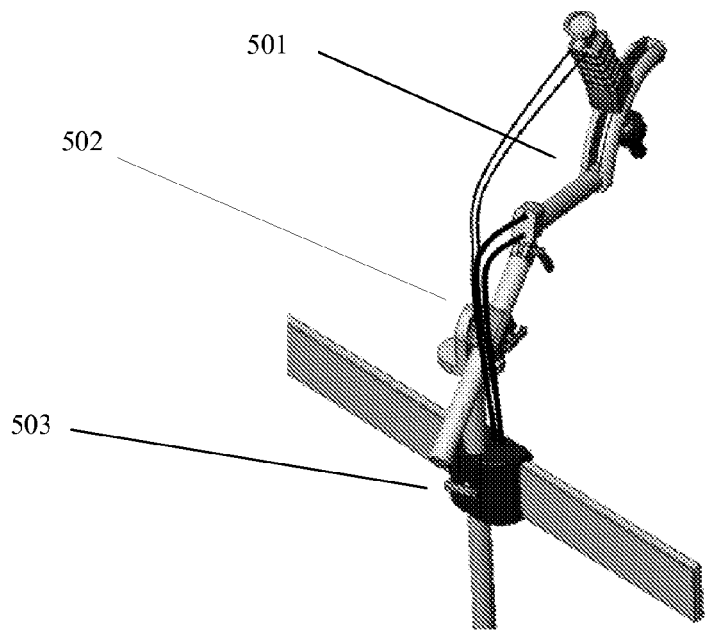
FIG. 10 presents a schematic and illustrated drawing of the entire system according to one embodiment of the present invention which comprises three main parts a manipulating endoscope mechanism (1); a force carriage system (2); and a manipulating system actuator (3)

Reference is now made to FIG. 10 which schematically represents the entire system according to one embodiment of the present invention. According to that embodiment, the system comprises three main parts: an endoscope manipulation mechanism (501); a force carriage system (502); and a force source (503). The endoscope manipulation mechanism may comprise cables, springs and/or rods. The force carriage system may comprise cables, chains, and/or rods as well. The force source comprises motors and/or may comprise actuators and pistons.

Figure 11:
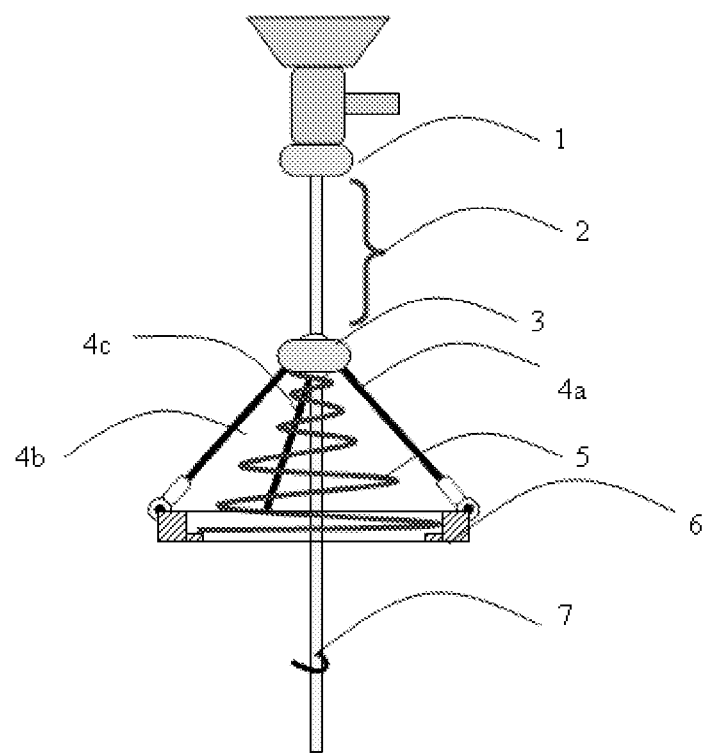
FIG. 11 presents a schematic illustration of the camera holder according to another embodiment of the present invention.
Figure 12:
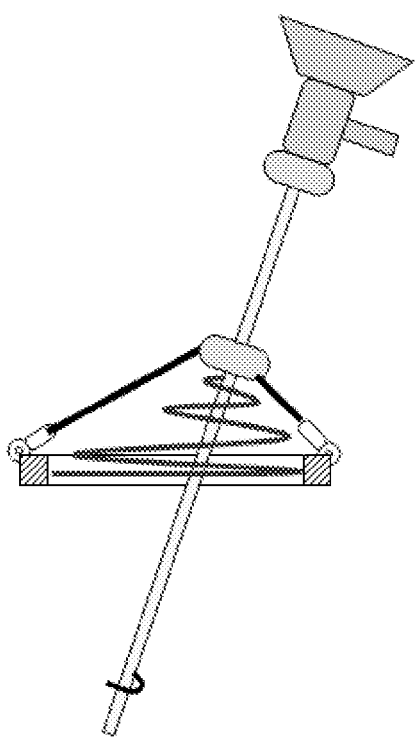
FIG. 12 is a schematic view of the camera holder illustrating the motion of the orientation ring relatively to the basis ring.

Reference is made now to FIG. 11, presenting a schematic illustration of the camera holder according to another embodiment of the present invention. The camera holder comprises a zoom ring 1; zoom mechanism 2; orientation ring 3; three cables, 4a, 4b and 4c having length of $L_1$, $L_2$ and $L_3$ respectively; a spring 5; and a basis ring 6. Also shown is the pinhole (7) in the operated body through which the endoscope is introduced. When the lengths of $L_1$ and $L_2$ are changed in conjunction with the spring resistance, the orientation ring is moved relative to the basis ring and get to an equilibrium point as illustrated in FIG. 12. Although a zoom action can be obtained by coordinated shortening of the cables $L_1$, $L_2$ and $L_3$ the mechanism includes an additional zoom option that acts independently of cable lengths $L_1$, $L_2$ and $L_3$.

Figure 13:
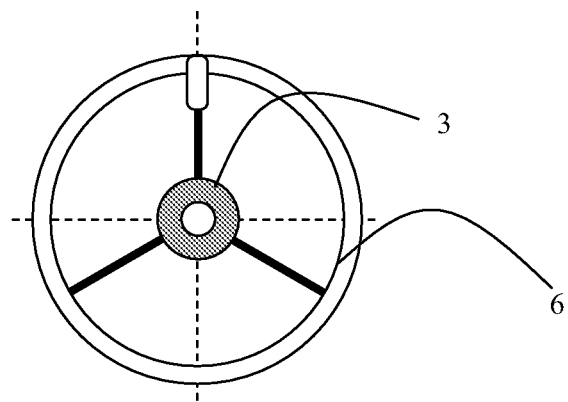
FIG. 13 is a schematic view of the orientation ring different position.

The different lengths of the cables when tensed, fix the place of the orientation ring as illustrated in FIG. 13. The mechanism controlling the cables length allows a shifting of the orientation cable and an inclination of the endoscope to a wanted angle. The endoscope has to rotate around its length axis whereas the surgeon operates without changing the orientation.

Figure 14:
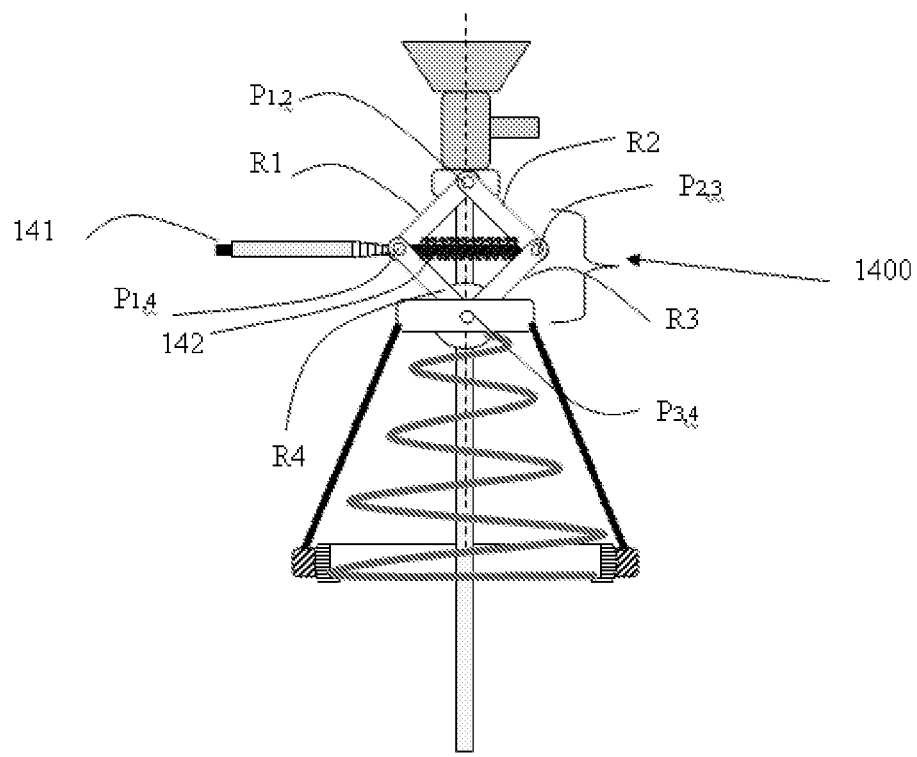
FIG. 14 is a schematic view of the "adjustment cable" zoom mechanism according to one embodiment of the present invention.

FIG. 14 schematically displays an "adjustment cable" zoom mechanism 1400 according to one embodiment of the present invention (alternative zoom mechanisms are displayed in FIGS. 18a, 18b, 19a, 19b, 20, 23 and 27 below). The zoom action is the endoscope movement in front and backward without changing the orientation. As can be seen from FIG. 14 the zoom mechanism additionally comprises an adjustment cable 141, 4 closed bar linkages R1, R2, R3, R4 comprising pivots $P_{1,2}$, $P_{2,3}$, $P_{3,4}$, $P_{1,4}$ with a linear spring containing the adjustment cable with a first end at pivot $P_{1,4}$ and the second end at pivot $P_{2,3}$.

Coupling spring 142 and adjustment cable 141 determine the distance between pivots $P_{1,2}$ and $P_{1,4}$, and hence determine the zoom position of the endoscope.

Figure 15:
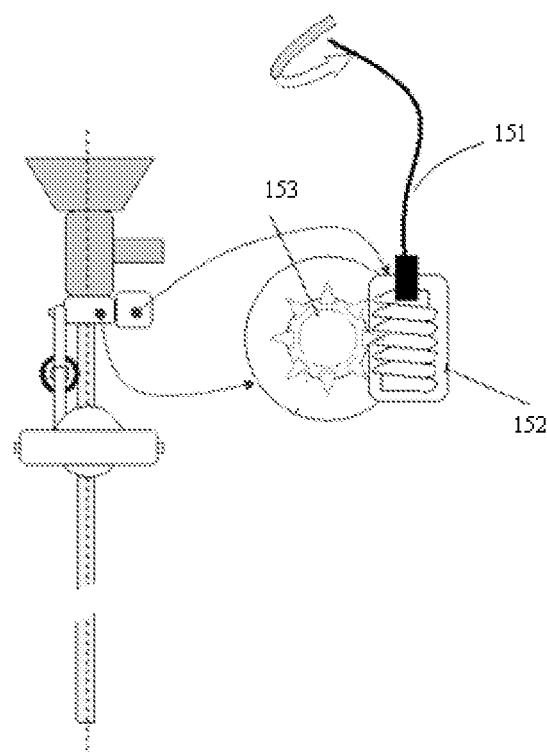
FIG. 15 presents a schematic description of the rotation mechanism.

Reference is made now to FIG. 15 presenting a schematic description of the rotation mechanism. As can be seen from FIG. 15, a rotating cable 151 is coupled to a worm gear 152 which is connected to the endoscope ring. When the cable rotates the worm gear 152, the cog which is connected to the endoscope ring 153, rotates and the endoscope passing through and rotates at the same amount.

Figure 16:
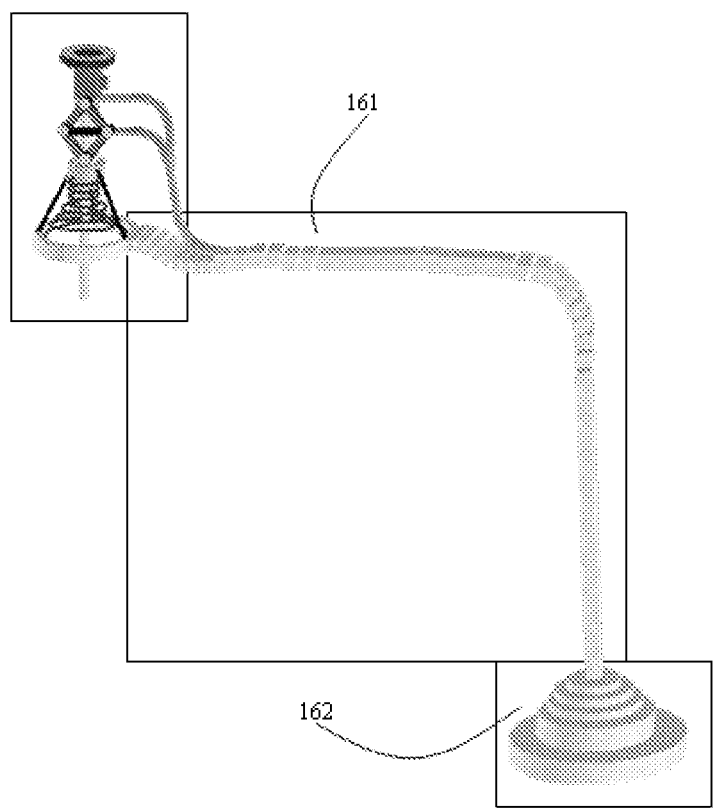
FIG. 16 represents the portable feature of the mechanism.
Figure 17:
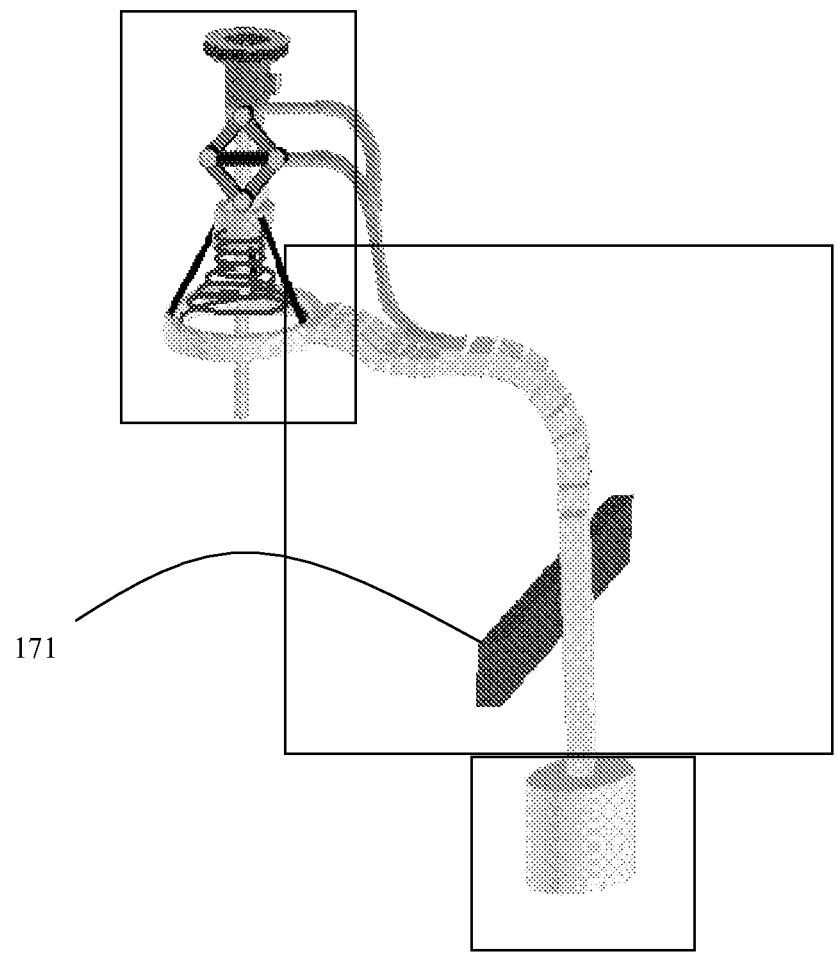
FIG. 17 is a schematic view of the mechanism placed beside a bed.

Reference is made now to the portable feature of the camera holder as described in FIG. 16. As shown in FIG. 16 the camera holder additionally comprises an adjustable arm 161 and a basis 162 including motors. The mechanism can be placed beside a bed using a track 171, as described in FIG. 17.

Figure 19A:
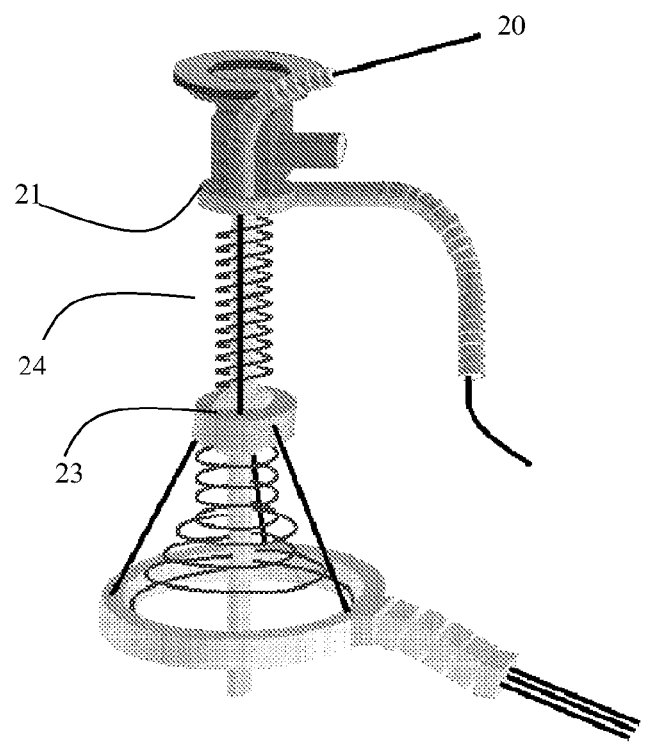
Figure 19B:
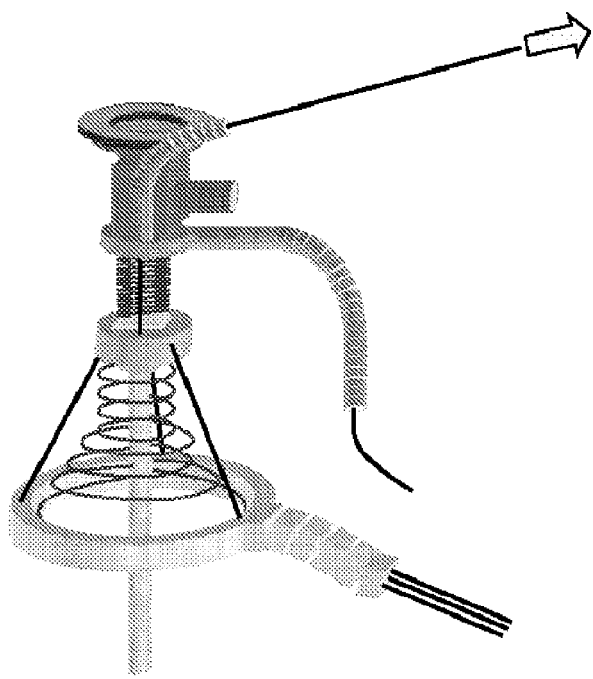
Figure 20:
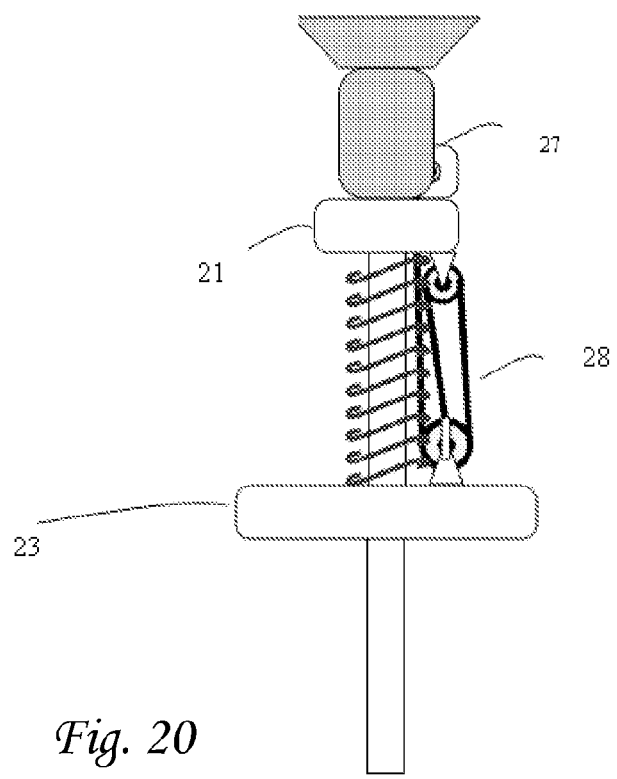
Figure 21:
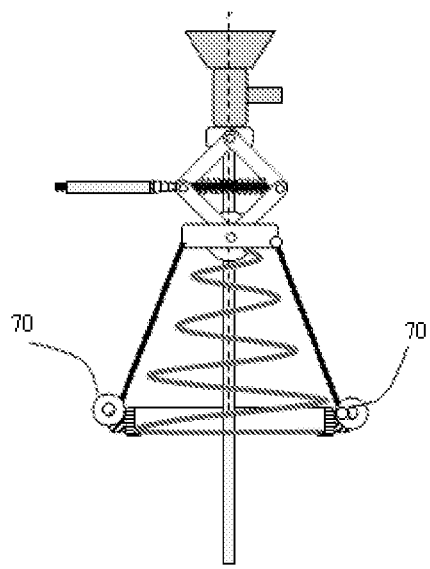
FIG. 21 presenting a schematic section view of the pulley blocks located on the endoscope motion mechanism.
Figure 22:
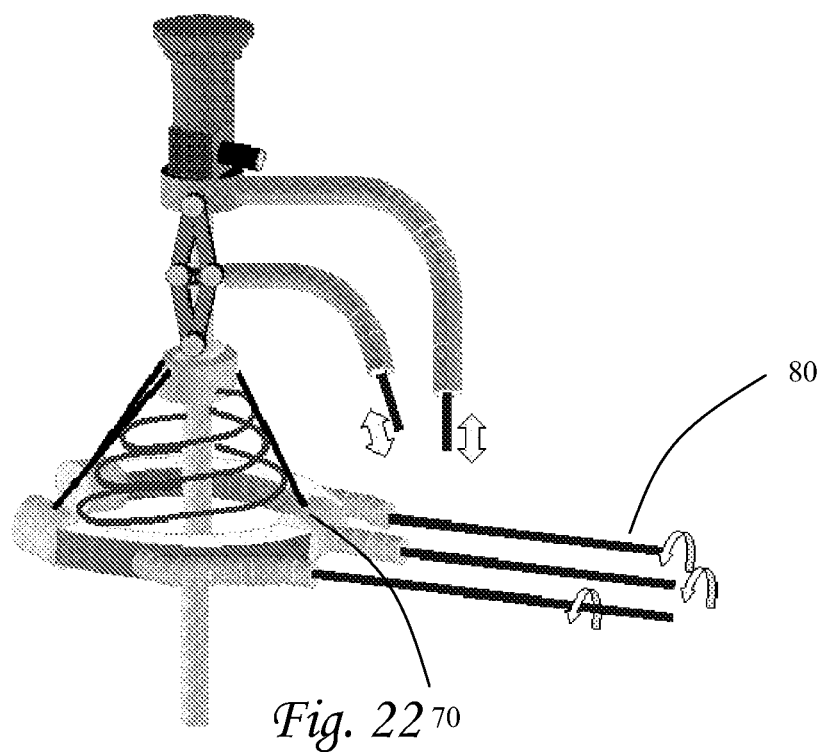
FIG. 22 is a three-dimension schematic view of FIG. 21.
Figure 23:
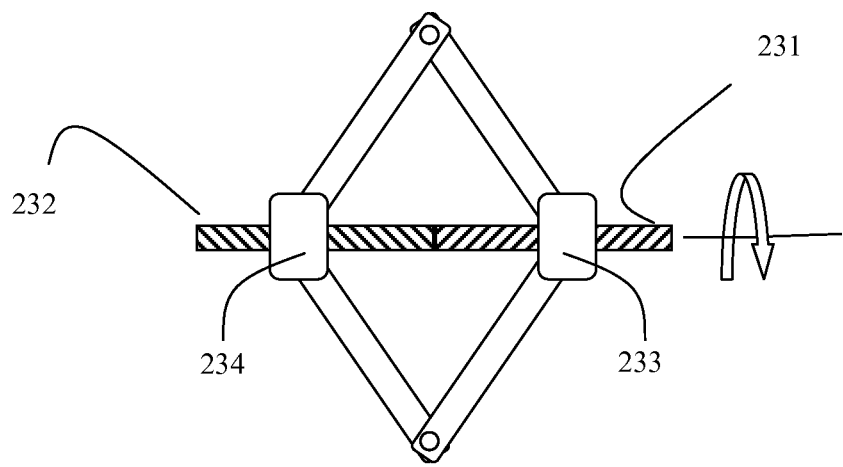
FIG. 23 is a schematic view of the "rotating cable" zoom mechanism obtained by rotating cable which turns a central screw with joins in different directions.

Reference is now made to FIGS. 18-23 which display a variety of zoom mechanisms according to different embodiments of the present invention. FIG. 18 displays a "parallelogram rods mechanism"; FIG. 19 displays "a spring mechanism" in which a spring connects the ring zoom and the orientation ring mechanisms; FIG. 20 displays a "reduction force mechanism"; FIGS. 21 and 22 present a mechanism in which the cable length is changed by means of pulley blocks; FIG. 23 presents a "rotating cable" zoom mechanism.

Figure 18A:
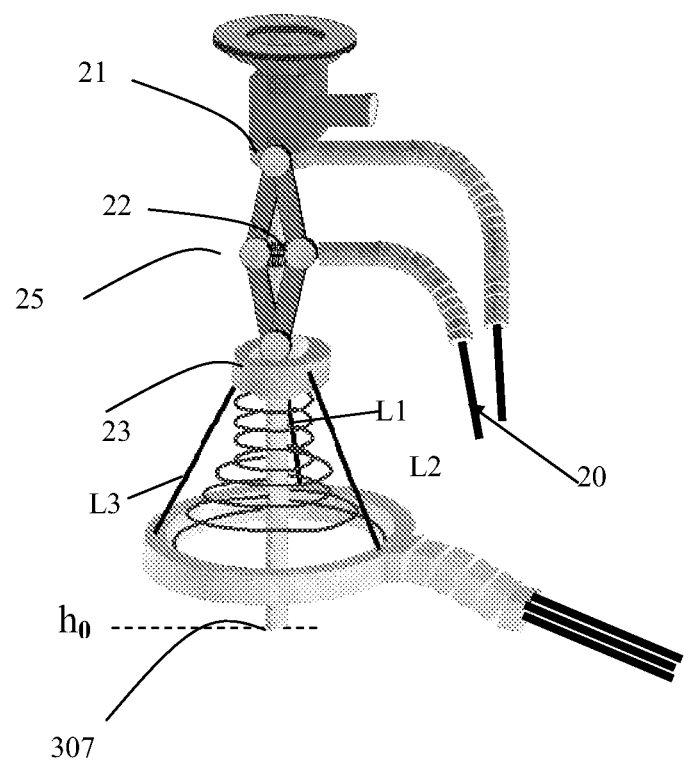
FIGS. 18a, 18b, 19a, 19b, 20 represent three different options for the zoom mechanism: 18 a and 18b with "parallelogram rods mechanism"; 19a and 19b with a "spring mechanism"; and 20 with a "reduction force device"
Figure 18B:
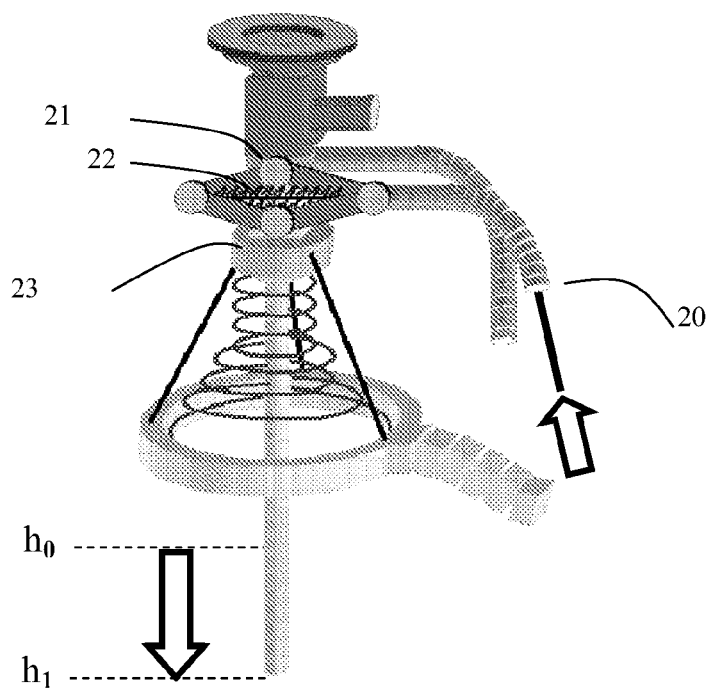

Reference is now made to FIGS. 18a and 18b which schematically display the zoom mechanism according to the "parallelogram rods mechanism".

As can be seen from FIGS. 18a and 18b the zoom mechanism comprises parallelogram rods 25, a spring 22, zoom ring 21, orientation ring 23 and a driving z cable 20.

At the first stage (FIG. 18a), the spring 22 is compressed. When the Z cable 20 is pulled the compressed spring 22 is released (see FIG. 18b) and the distance between the zoom ring 21 and the orientation ring 23 is reduced. In this manner the zoom movement is produced and the endoscope 307 is moved from position $h_0$ to position $h_1$. Releasing and pulling the driving Z cable 20 allows continuous deep fixing of the zoom. A tiny motor wraps the Z cable. The stake system allows on one hand a reduction of the force required to compress the spring, and on the other hand augmentation of the zoom movement sensitivity. In order to obtain a small zoom movement for each turn of the motor, many windings of the Z cable are required.

Reference is now made to FIGS. 19a and 19b which schematically display a "spring" zoom mechanism according to another embodiment of the invention. As can be seen from FIGS. 19a and 19b the zoom mechanism comprises a ring zoom 21, an orientation ring 23 and a spring 24 which connects the ring zoom 21 and the orientation ring 23. In the "spring zoom mechanism," when the z-cable 20 is pulled, spring 24 is compressed, and the distance between the ring zoom 21 and the orientation ring 23 is reduced.

Reference is now made to FIG. 20 which schematically displays the "reduction force mechanism" according to another embodiment of the present invention. As can be seen from FIG. 20, the zoom mechanism comprises a motor 27, a ring zoom 21, an orientation ring 23 and a reduction force device 28 which connects the ring zoom 21 and the orientation ring 23.

Reference is now made to FIGS. 21 and 22 which display another mechanism for changing the cable's length, in which the change in the cable's length change is based on the motion of pulley blocks 70. The pulley blocks are located on the endoscope motion mechanism. FIG. 21 presents a schematic section view of this. The pulley block 70 contains a drum with an axle and a wire. The pulley block may be operated by any kind of rigid or flexible shaft. This kind of structure demonstrates another embodiment using the same principle: controlling the spatial angular position of the endoscope by using a combination of the lengths of the wires. The pulley block may have some advantages in respect to the mechanisms of wrapping the wires that pass through the adjusting arm as described before.

In FIG. 22, a three-dimensional schematic illustration is presented, in which wire 80 that activates the rotation mechanism is also shown.

Reference is now made to FIG. 23, which displays the "rotating cable" zoom mechanism. Realization of the zoom mechanism can be done by rotating a cable which turns a central screw comprising two different screws with opposite orientations: screw R 231 and screw L 232 when the central zoom is rotated to a first direction; as a non-limiting example, if the cable is turned clockwise, nuts 233 and 234 become closer and the endoscope moves in a zoom up movement.

When the central zoom is rotated in a second direction (counterclockwise in this case), the distance between the nuts increases and the endoscope moves in a zoom down movement as illustrated in FIG. 23.

Figure 24:
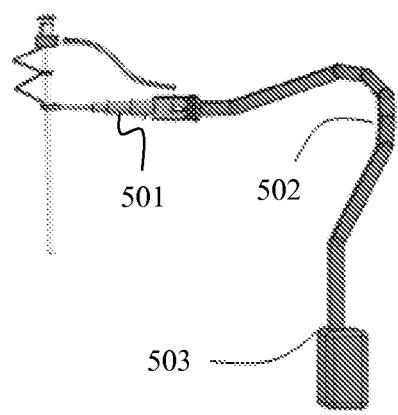
FIG. 24 presents a schematic and illustrated drawing of the entire system according to one embodiment of the present invention which comprises three main parts a manipulating endoscope mechanism (1); a force carriage system (2); and a manipulating system actuator (3)
Figure 25:
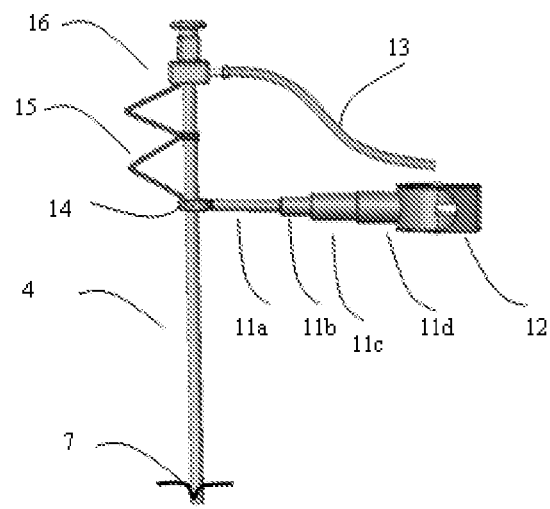
FIG. 25 presents a schematic illustration of the manipulating endoscope mechanism (1)

Reference is made now to FIGS. 24 and 25, presenting a schematic drawing of the entire device according to another embodiment of the present invention. As can be seen from FIG. 24 the device comprises inter alia an endoscope manipulation mechanism (501); a force carriage system (502); and a manipulating system actuator or a force source (503). FIG. 25 presents a schematic illustration of the manipulating endoscope mechanism (501). The mechanism comprises inter alia a rotating link (12); linear links (11a, b, c, d); a gimbal ring mechanism (14); zoom leading bars (15); zoom and rotation endoscope mechanism (16); cables tubes (13). The pinhole in the operated body is illustrated by 7, where the endoscope 4 passes through into the abdomen cavity.

Figure 26:
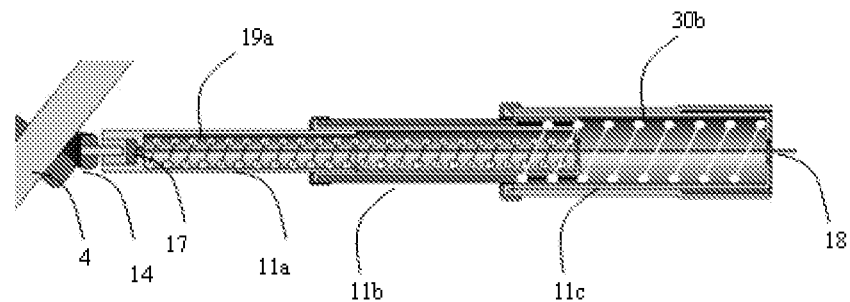
FIG. 26 presents a schematic cut view along the sliding links 11a, 11b, 11c of FIG. 25.

Reference is made now to FIG. 26, presenting a schematic cut view along the sliding links 11a,b,c. The cable head 17 is mounted in a hole at the head of link 11a. When the links 11a is pulled by cable 18 it slide into links 11b against the pushing force of springs 19 a, b and therefore the distance between the center of the gimbal ring mechanism 14 and the center of the rotating link 12 becomes shorter. When the cable 18 is released, spring 19a push links 11a out of links 11b and 11b out of links 11c, and the distance between the center of the gimbal ring mechanism 14 and the center of the rotating link 12 becomes longer; in both cases the gimbal (50) is moved relative to the pinhole, changing the orientation of the endoscope. When the cable does not move, equilibrium is kept at every point by the pushing forces of the springs that tend to push the link outward, and the cable tension. The zoom action is essential in laparoscopic surgery. Changing the zoom enables the surgeon to see important details of the operated organs e.g. "zoom in", and to examine the general situation of the operation status when moving the endoscope away from the scenery e.g. "zoom out". Another important feature is the ability to make a zoom movement while keeping the center of the picture without movement. This could be achieved if the zoom movement is done without changing the endoscope orientation.

Figure 28A:
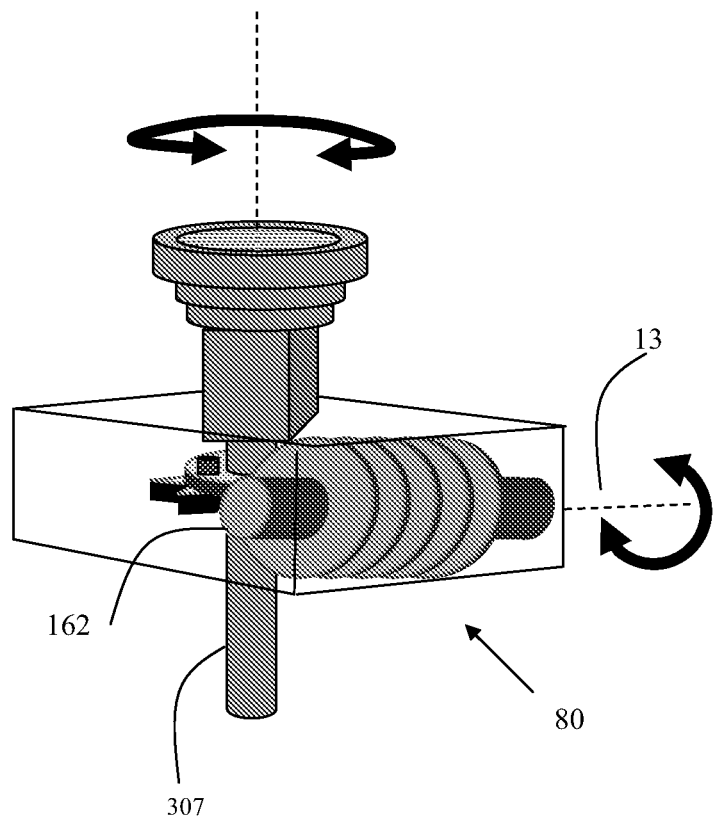
FIGS. 28a, 28b and 28c schematically present the rotation mechanism according to another embodiment of the present invention.
Figure 28B:
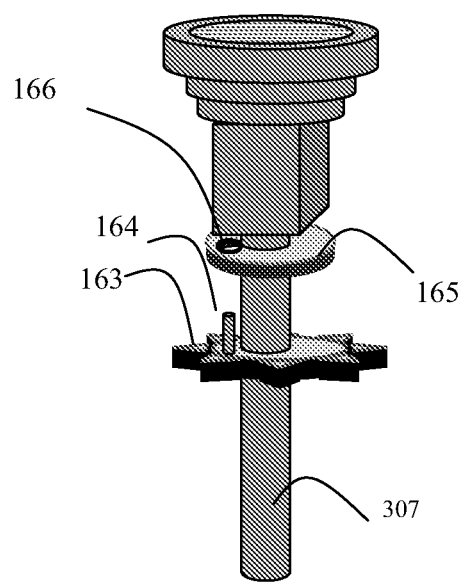
Figure 28C:
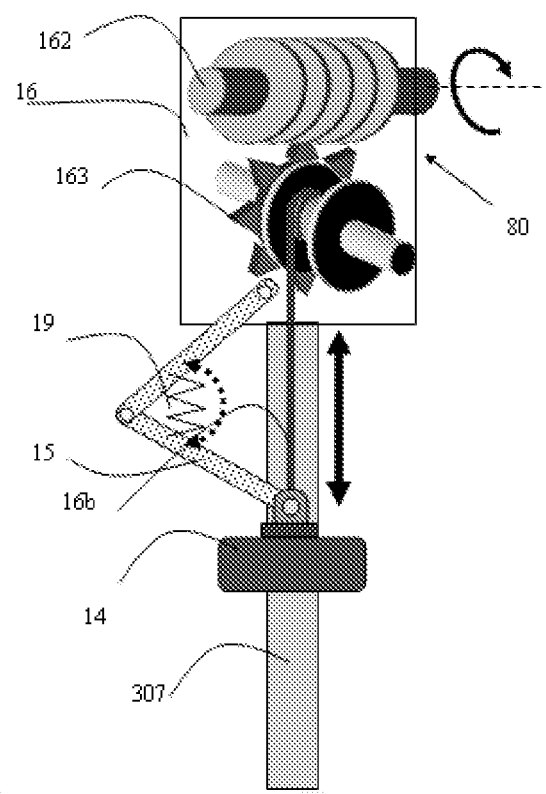

Reference is made now to FIGS. 28a, 28b and 28c presenting schematically another principal mechanism that controls the linear movement of the endoscope e.g. "zoom in", and "zoom out". FIGS. 28a, 28b and FIG. 28c also present the rotation mechanism (80), filling the needs mentioned above, and also allowing fast removal of the endoscope in order to clean its lens. Cog wheel 163 allows the endoscope rod 307 to cross through its center and to make rolling and sliding movements. Peg 164 originates at the upper surface of cog wheel 163. A disk 165 is tightened to the endoscope rod 4. While assembling the endoscope, the upper wall of the box 16 is opened and the endoscope is entered through cog-wheel 163 center, into a hole in the lower wall and through ring e.g. gimbal ring mechanism 14 until the peg 164 is threaded into aperture 166 of disk 165. Then the upper wall of box 16 is closed, keeping the endoscope from moving out of box 16, to ensure coupling between the endoscope and the entire zoom mechanism. The rotation of the endoscope along is achieved by rotating the screw 162 that moves cog-wheel 163 and the endoscope 307 via coupled disk 165. The source of the movement of screw 162 can be a rotating cable transmitting the rotation movement from "remote" motor or small motor placed in or near box 16. When needed, the mechanism described above allows quick disassembling of the endoscope out of the zoom mechanism without changing any degree of freedom of its spatial position. This property is important because the surgeon does not have to deal with re-positioning of the system. This property is achieved because the endoscope 307 does not have any role in keeping the position of the entire zoom mechanism. The equilibrium between links 15, springs 19 and cable 16a maintain depth of the zoom and constrain of relation between the peg 164 and hole 166 keeps the angle of rotation. When the endoscope is assembled again, the endoscope retrieves its original spatial position.

Reference is made now to FIGS. 28a, 28b and 28c presenting schematically another principal mechanism that controls the linear movement of the endoscope e.g. "zoom in", and "zoom out". FIGS. 28a, 28b and FIG. 28c also present the rotation mechanism (80), filling the needs mentioned above, and also allowing fast removal of the endoscope in order to clean its lens. Cog wheel 163 allows the endoscope rod 307 to cross through its center and to make rolling and sliding movements. Peg 164 originates at the upper surface of cog wheel 163. A disk 165 is tightened to the endoscope rod 4. While assembling the endoscope, the upper wall of the box 16 is opened and the endoscope is entered through cog-wheel 163 center, into a hole in the lower wall and through ring e.g. gimbals 14 until the peg 164 is threaded into aperture 166 of disk 165. Then the upper wall of box 16 is closed, keeping the endoscope from moving out of box 16, to ensure coupling between the endoscope and the entire zoom mechanism. The rotation of the endoscope along is achieved by rotating the screw 162 that moves cog-wheel 163 and the endoscope 307 via coupled disk 165. The source of the movement of screw 162 can be a rotating cable transmitting the rotation movement from "remote" motor or small motor placed in or near box 16. When needed, the mechanism described above allows quick disassembling of the endoscope out of the zoom mechanism without changing any degree of freedom of its spatial position. This property is important because the surgeon does not have to deal with re-positioning of the system. This property is achieved because the endoscope 307 does not have any role in keeping the position of the entire zoom mechanism. The equilibrium between links 15, springs 19 and cable 16a maintain depth of the zoom and constrain of relation between the peg 164 and hole 166 keeps the angle of rotation. When the endoscope is assembled again, the endoscope retrieves its original spatial position.

For example, in the embodiment of this invention shown in FIG. 28b, cog wheel 2 (denoted as 77) may rotate via pin that passes through a hole in a ring that is attached directly to the endoscope, by the force of friction. When cog wheel 2 (77) rotates, the ring rotates and the endoscope rotates also in the same directions.

Figure 29:
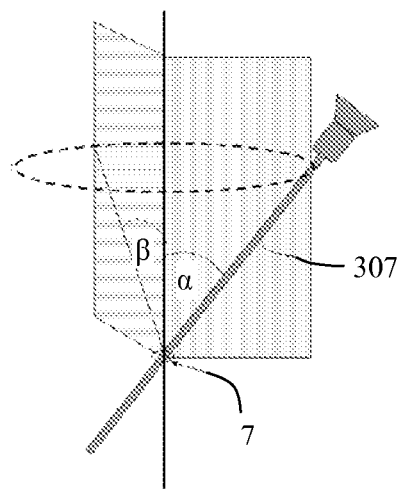
FIG. 29 schematically presents the envelope of the endoscope range of movement.

While executing the operation the surgeon must be able to move the endoscope to any desired orientation. The envelope of the endoscope range of movement is shown in FIG. 29.

The ability to rotate along the endoscope long axis is essential in laparoscopic surgery. While rotating the endoscope through the insertion point 7 in order to change the endoscope orientation e.g. combination of angle α and angle β shown at FIG. 29, a component of the angular change may be not along the long axis of the endoscope. This angular component may cause undesirable rotation of the endoscope, which in result, cause annoying rotating movement of the picture as viewed on the surgeon's video screen. In a traditional laparoscopic operation, the person that holds the endoscope, intuitively, makes the needed changes to keep the operation scenery without undesirable rotation e.g., keeping the moving picture parallel to it self at all time.

Figure 30:
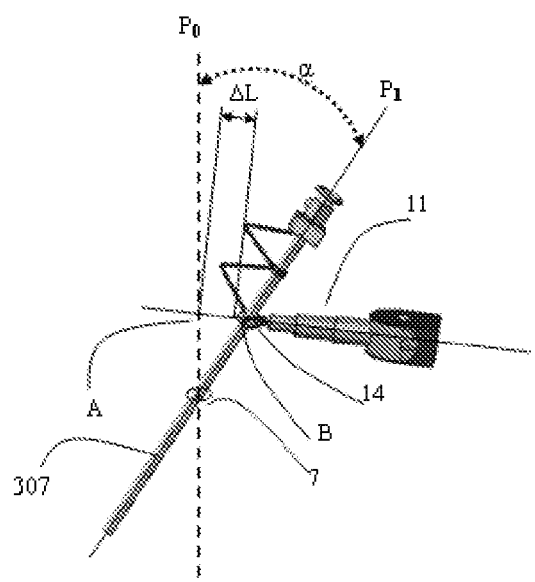
FIG. 30 schematically presents the way the mechanism acts to controls one angle of the endoscope by changing the total length of the telescopic arm.

Reference is made now to FIG. 30, presenting schematically the way the mechanism acts to control one angle of the endoscope by changing the total length of the telescopic arm.

FIG. 30 shows the angular movement of endoscope 307 that was at starting position P0 e.g. α=0. Activating the sliding mechanism causes the movement of gimbal ring mechanism 14 from point A to point B causing endoscope 4 to rotate about the insertion point 7, to a desired position P1. While the combined shortening of links 11a, b, c, the distance between gimbal ring mechanism 14 and the insertion point 7 changes, causing an undesired zoom movement. The distance of this movement can be calculated by solving the triangle AB7 (e.g. by using the law of cosines given angle α) and compensated by a controlled zoom motion that advances or retracts endoscope 307 by the amount necessary to place the endoscope in the position in which it would have been had the distance between the gimbal (50) and the insertion point not changed.

Figure 31:
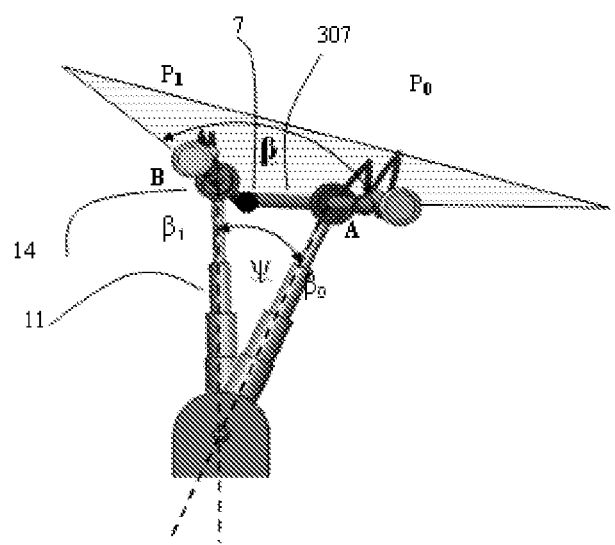
FIG. 31 schematically presents the way the mechanism acts to controls another angle (β) of the endoscope by rotating telescopic arm.

Reference is made now to FIG. 31, schematically presenting the way the mechanism acts to control another angle e.g. β of the endoscope by rotating telescopic arm. FIG. 31 shows the angular movement of endoscope 307 that was at starting position $P_0$. Activating the rotating mechanism causes the movement of gimbal ring mechanism 14 in a radial movement, from point A to point B e.g. angle ψ, causing endoscope 307 to rotate about the insertion point 7, by angle β, to a desired position P1. While the rotating of arm 11, the distance between gimbals 14 and the insertion point 7 changes, causing an undesired zoom movement. The distance of this movement can be calculated and compensated by a controlled zoom motion performed in a manner analogous to that explained previously. The combination of the two independent movements of the mechanism arm enables the surgeon to move the endoscope to any orientation, and reach any desired point within the working envelope.

Figure 32A:
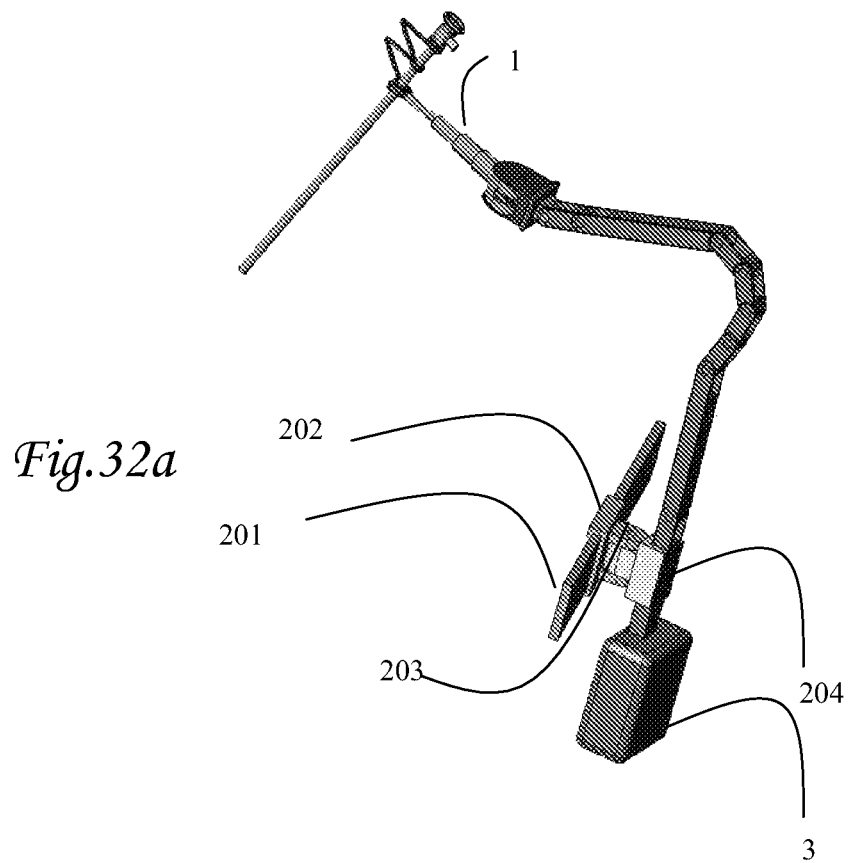
FIG. 32a schematically presents the portable feature of the mechanism.
Figure 32B:
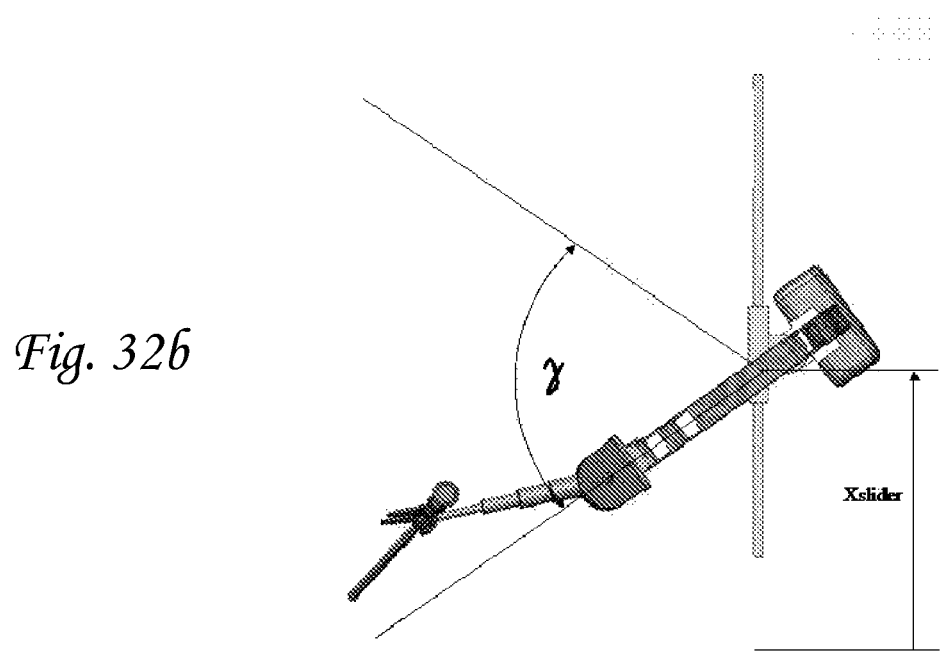
FIG. 32b schematically presents an upper view of the position abilities of the system: the rotation angle γ, and the horizontal position X slider.

Reference is made now to the portable feature of the mechanism as described in FIG. 32a. The mechanism is placed beside a bed, on track 201, and can be placed at any point along track 201 by moving slider 202; in order to achieve the necessary position the surgeon can also rotate the system around pivot 203 and to change the height by sliding the system along house 204. FIG. 32b shows schematically an upper view of the positioning abilities of the system: the rotation angle γ, and the horizontal position X slider.

The invention claimed is:

1. A camera holder for use in laparoscopic surgery, comprising:
   a. a pivoting support adapted to be pivotally attached to an endoscope; said pivoting support being for enabling said endoscope to pivot around said pivoting support; and,
   b. a mechanism for moving said pivoting support independently in two arc-shaped paths, said mechanism mechanically connected to said pivoting support, thereby enabling said endoscope to rotate around an insertion point into a body of a subject; said endoscope pivotally attached to said camera holder can pivot at said insertion point independent of the distance between said pivoting support and said insertion point, wherein said mechanism for moving said pivoting support independently in said two arc-shaped paths, moves said pivoting support in two planes along an arc shaped guide disposed within an arc shaped housing in which said mechanism moves said pivoting support, said arc shaped housing comprising a base, said base comprising a housing containing a lead screw (15) constrained to remain in one position, rotation of said lead screw moving a nut (10) through which the screw is threaded moving the nut; said moving nut physically connected to a gimbal (50) with links (20) adapted to transfer linear movement of the nut to said gimbal resulting in movement of said gimbal back and forth along the arc shaped guide, whereby a sliding degree of freedom is obtained.

2. The camera holder according to claim 1, further comprising:
   a. a housing (309) attachable to an endoscope via said pivoting support, said housing comprising:
      i. at least one zoom mechanism;
      ii. at least one endoscope rotation mechanism; and,
   b. at least one sliding degree of freedom (305).

3. The camera holder according to claim 2, wherein said camera holder additionally comprises:
   a. a motor house (301);
   b. means adapted to transmit movement to said zoom mechanism;
   c. means adapted to transmit movement to said endoscope rotation mechanism;
   d. means adapted to transmit movements to said sliding degree of freedom.

4. The camera holder according to claim 3, wherein said camera holder additionally comprises a quick release handle adapted to disassemble said endoscope out of said housing without changing any of said degrees of freedom.

5. The camera holder according to claim 1, wherein said camera holder additionally comprises (a) at least one adjustable arm; and (b) a basis comprising at least one motor; wherein said adjustable arm couples said camera holder and said basis.

6. The camera holder of claim 1, wherein said mechanism for moving said pivoting support in said two arc-shaped paths comprises a curved guide for guiding said pivoting support in a first arc-shaped path and a force source (503) for moving said pivoting support in a second arc-shaped path.

7. The camera holder of claim 6, wherein said second arc-shaped path is orthogonal to said first arc-shaped path.

8. The camera holder of claim 6, wherein said pivoting support includes at least one gimbal.

* * * * *